United States Patent
Kameda et al.

(10) Patent No.: US 11,719,706 B2
(45) Date of Patent: Aug. 8, 2023

(54) METHOD FOR MEASURING A BIOMARKER IN A BIOLOGICAL SAMPLE OF AN IPAF PATIENT

(71) Applicants: SAPPORO MEDICAL UNIVERSITY, Sapporo (JP); SYSMEX CORPORATION, Kobe (JP)

(72) Inventors: Masami Kameda, Sapporo (JP); Mitsuo Otsuka, Sapporo (JP); Takehiro Hasegawa, Kobe (JP)

(73) Assignees: SAPPORO MEDICAL UNIVERSITY, Sapporo (JP); SYSMEX CORPORATION, Kobe (JP)

( * ) Notice: Subject to any disclaimer, the term of this patent is extended or adjusted under 35 U.S.C. 154(b) by 439 days.

(21) Appl. No.: 16/847,994

(22) Filed: Apr. 14, 2020

(65) Prior Publication Data

US 2020/0341008 A1    Oct. 29, 2020

(30) Foreign Application Priority Data

Apr. 25, 2019 (JP) ................ 2019-084223

(51) Int. Cl.
*G01N 33/68* (2006.01)

(52) U.S. Cl.
CPC ..... *G01N 33/6893* (2013.01); *G01N 33/6863* (2013.01); *G01N 2333/7158* (2013.01); *G01N 2800/12* (2013.01)

(58) Field of Classification Search
CPC ........... G01N 2800/12; G01N 33/6893; G01N 33/6863; G01N 2333/7158
See application file for complete search history.

(56) References Cited

FOREIGN PATENT DOCUMENTS

| JP | 2013-509869 A | 3/2013 |
| WO | 2014/144564 A2 | 9/2014 |
| WO | 2014/148429 A1 | 9/2014 |

OTHER PUBLICATIONS

Fisher et al. "An official European Respiratory Society/ American Thoracic Society research statement: interstitial pneumonia with autoimmune features", Jul. 9, 2015, European Respiratory Journal, vol. 46, p. 976-987. (Year: 2015).*
Zhou et al. "CD4 T Helper Cell Subsets and Related Human Immunological Disorders", Oct. 28, 2020, International Journal of Molecular Sciences, vol. 21, p. 1-26. (Year: 2020).*
Kishi et al. "Pathogenesis of cBFL in common with IPF? Correlation of IP-10/TARC ratio with histological patterns", Feb. 13, 2008, Thorax, vol. 63, p. 810-816. (Year: 2008).*
Miadlikowska et al. "Review: Serum Biomarkers of Lung Fibrosis in Interstitial Pneumonia with Autoimmune Features—What Do We Already Know?", Dec. 24, 2021, Journal of Clinical Medicine, 11, 79, p. 1-11. (Year: 2021).*

(Continued)

*Primary Examiner* — Gary B Nickol
*Assistant Examiner* — Amelia Nicole Dickens
(74) *Attorney, Agent, or Firm* — Sughrue Mion, PLLC

(57) ABSTRACT

Disclosed is a method for measuring a biomarker in a biological sample of the IPAF patient, wherein the biomarker comprises at least one selected from the group consisting of CXCL9 and CXCL10, and a measurement result of the biomarker is used as an index for determining treatment responsiveness to anti-inflammatory therapy.

4 Claims, 13 Drawing Sheets

(56) References Cited

OTHER PUBLICATIONS

Oda et al. "Chemokine profiles of interstitial pneumonia in patients with dermatomyositis: a case control study", May 9, 2017, Scientific Reports, 7: 1635, p. 1-10. (Year: 2017).*

Oldham et al. "Characterisation of patients with interstitial pneumonia with autoimmune features", Apr. 21, 2016, Eur Respir J, vol. 47, p. 1767-1775. (Year: 2016).*

Richards et al. "Characterization and Peripheral Blood Biomarker Assessment of Jo-1 Antibody-Positive Interstitial Lung Disease", Jul. 2009, Arthritis Rheum, 60(7): 2183-2192. Available from PMC p. 1-17. (Year: 2009).*

M. Chen, et al., "Measurement of cytokines and chemokines and association with clinical severity of dermatomyositis and clinically amyopathic dermatomyositis", British Journal of Dermatology (2018) 179, pp. 1334-1341.

T. J. Richards, Ph.D. et al., "Characterization and Peripheral Blood Biomarker Assessment of Jo-1 Antibody-Positive Interstitial Lung Disease", National Institutes of Health, Arthritis Rheum, Author manuscript, available in PMC Jul. 1, 2010.

M. Hirakata, "Autoantibody in polymyositis and dermatomyositis" and translation, Medical Education Center/ Department of Internal Medicine, Keio University School of Medicine, Clin Rheumatol, 25, pp. 149-158, 2013.

S. Makino, "Interstitial pneumonia in collagen disease" and translation, Osaka Medical College, 1$^{st}$ Department of Internal Medicine, Clin Rheumatol, 24, pp. 165-171, 2012.

Extended European Search Reported dated Oct. 5, 2020 in European Application No. 20 17 0913.

Rekha Vij et al.: "Autoimmune-featured interstitial lung disease: a distinct entity", Chest, vol. 140, No. 5, Nov. 1, 2011, pp. 1292-1299 (8 pages total).

Adelle Jee et al.: "Role of Autoantibodies in the Diagnosis of Connective-Tissue Disease ILD (CTD-ILD) and Interstitial Pneumonia with Autoimmune Features (IPAF)", Journal of Clinical Medicine, May 4, 2017, 6(5):51, pp. 1-21 (21 pages total).

Katsuhiro Oda et al.: "Chemokine profiles of interstitial pneumonia in patients with dermatomyositis: a case control study", Scientific Reports, May 9, 2017, 7(1): 1635, pp. 1-10 (10 pages total).

Japanese Office Action dated Jan. 31, 2023 in Japanese Application No. 2019-084223.

Japanese Office Action dated Apr. 4, 2023 in Japanese Application No. 2019-084223.

* cited by examiner

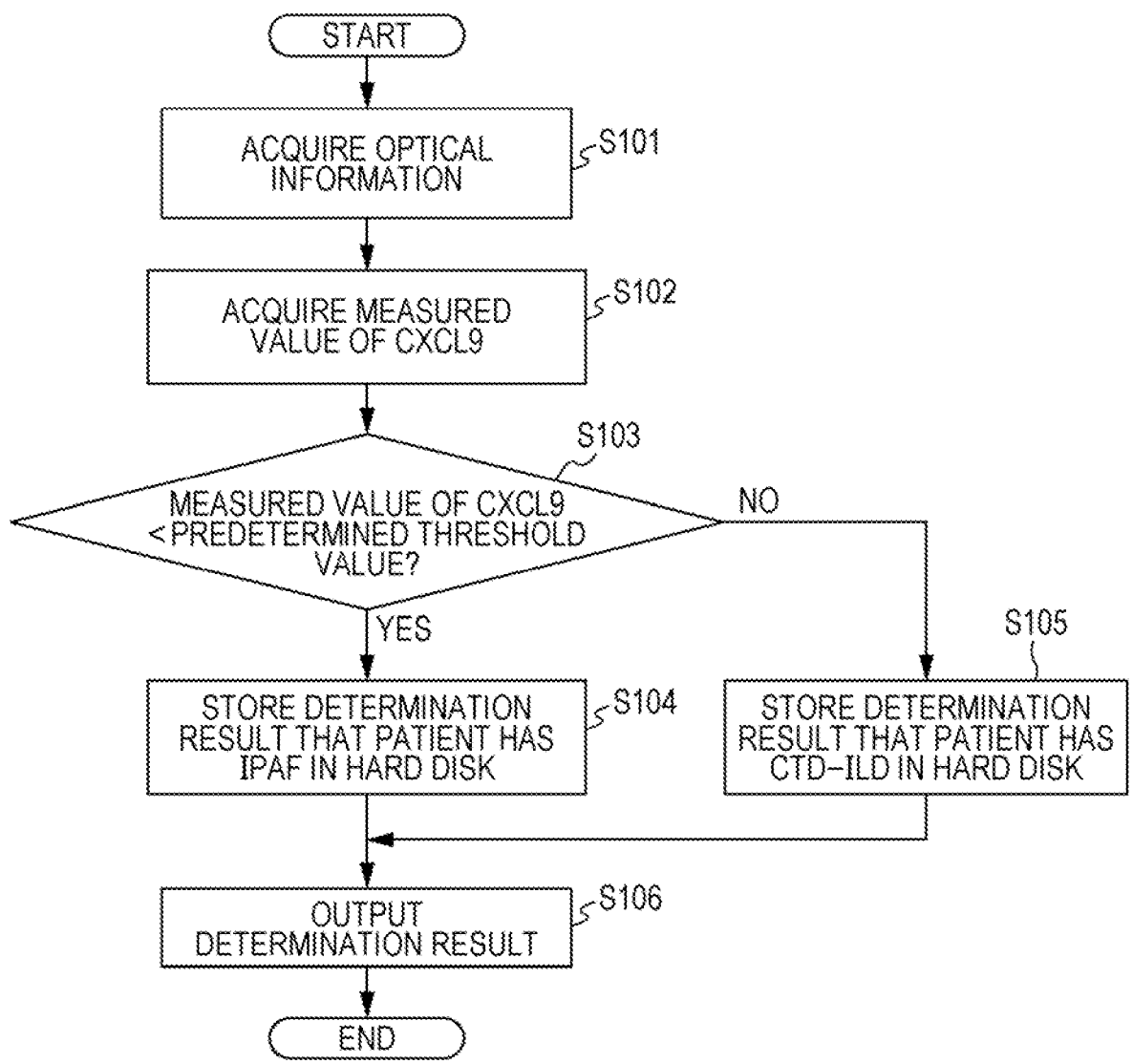

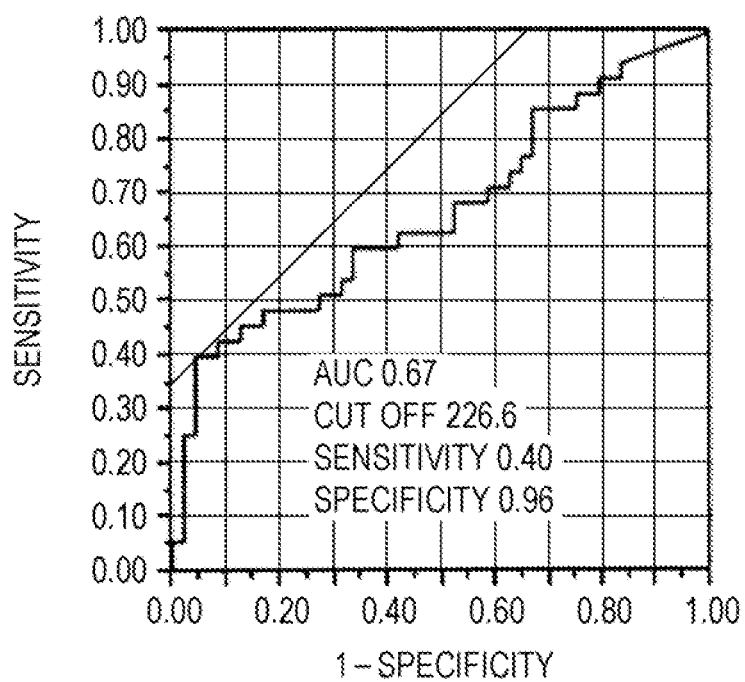

METHOD FOR MEASURING A BIOMARKER IN A BIOLOGICAL SAMPLE OF AN IPAF PATIENT

CROSS REFERENCE TO RELATED APPLICATIONS

This application claims priority from prior Japanese Patent Application No. 2019-084223, filed on Apr. 25, 2019, entitled "Method for acquiring information on condition of patient with interstitial pneumonia and use thereof", the entire contents of which are incorporated herein by reference.

TECHNICAL FIELD

The present invention relates to a method for measuring a biomarker in a biological sample of an IPAF patient.

BACKGROUND

Interstitial pneumonia is a disease in which inflammation and fibrosis occur in the interstitial tissue of the lung, especially in the alveolar septum. As interstitial pneumonia progresses, lung fibrosis causes a decrease in vital capacity and gas exchange capacity, and symptoms of dyspnea appear. There are many causes of interstitial pneumonia. For example, interstitial pneumonia that causes collagen disease as an underlying disease is called connective tissue disease associated interstitial lung disease (CTD-ILD). Interstitial pneumonia of unknown cause without underlying disease and the like is called idiopathic interstitial pneumonia (IIPs). Treatment of interstitial pneumonia differs between CTD-ILD and IIPs. Anti-inflammatory therapy is mainly used for CTD-ILD, and immunosuppressants such as steroids are used. Anti-inflammatory therapy is rather not provided for idiopathic pulmonary fibrosis (IPF), a disease that accounts for a majority of IIPs, and antifibrotic drugs such as pirfenidone are used.

Discrimination between CTD-ILD and IIPs is performed by physical findings such as skin and joints and blood tests such as autoantibodies. CTD-ILD satisfies diagnostic criteria for each collagen disease, and shows pulmonary lesions peculiar to interstitial pneumonia. In IIPs, no specific physical findings, autoantibodies or the like are found for collagen disease. In addition, there is also a report suggesting that it is possible to discriminate between interstitial pneumonia associated with some collagen diseases and IPF, by measurement of biomarkers in blood. Specifically, Richards T. J. et al., Characterization and Peripheral Blood Biomarker Assessment of Jo-1 Antibody-Positive Interstitial Lung Disease, Arthritis Rheum., 2009, vol. 60, p. 2183-2192 describes that CXC chemokine ligand 9 (CXCL9) and CXC chemokine ligand 10 (CXCL10) concentrations in serum of patients with anti-Jo-1 antibody positive interstitial pneumonia are significantly higher than in IPF patients. The anti-Jo-1 antibody refers to an autoantibody specific to polymyositis/dermatomyositis (PM/DM), which are one of collagen diseases.

However, in actual clinical practice, discrimination between CTD-ILD and IIPs is not easy. One of the causes is that, among the interstitial pneumonia, there are cases where symptoms related to collagen disease, physical findings, autoantibodies and the like are observed, but diagnostic criteria for collagen disease are not satisfied. Such cases have characteristics of suspected collagen disease, but had to be classified as IIPs. However, in 2015, the European Respiratory Society (ERS) and the American Thoracic Society (ATS) proposed a new concept called Interstitial pneumonia with autoimmune features (IPAF) and its diagnostic criteria (see Fischer A. et al., Eur Respir J., 2015, vol. 46, p. 976-987). The diagnostic criteria for IPAF required that one or more items in at least two domains of clinical, serologic and morphological domains be satisfied. In the clinical domain, whether there are symptoms specific to collagen disease in fingers and joints is confirmed. In the serological domain, whether autoantibodies specific to collagen disease are observed is confirmed. In the morphological domain, whether a predetermined pattern of interstitial pneumonia is observed in a tissue obtained by a high-resolution CT image or a lung biopsy is confirmed.

The diagnostic criteria for IPAF require diagnosis by doctors in multiple specialties such as collagen disease internal medicine, respiratory medicine, and diagnostic pathology. Therefore, for example, it is difficult for a doctor in respiratory medicine alone to discriminate between IPAF and CTD-ILD. In addition, cases in which pulmonary lesions are observed prior to collagen disease also make discrimination diagnosis difficult. In other words, even when once diagnosed as IIPs, symptoms related to collagen disease may appear during the course and IPAF or CTD-ILD may be suspected. Although autoantibodies specific to each collagen disease and the like are known, no biomarker useful for discrimination between IPAF and CTD-ILD is currently known. In view of such circumstances, an object of the present invention is to provide a means for enabling discrimination of condition of a patient with interstitial pneumonia.

SUMMARY OF THE INVENTION

The scope of the present invention is defined solely by the appended claims, and is not affected to any degree by the statements within this summary.

The present invention provides a method for measuring a biomarker in a biological sample of the IPAF patient, wherein the biomarker comprises at least one selected from the group consisting of CXCL9 and CXCL10, and a measurement result of the biomarker is used as an index for determining treatment responsiveness to anti-inflammatory therapy.

The present invention provides a method for treating an interstitial pneumonia patient with anti-inflammatory therapy, comprising:

measuring at least one biomarker in a biological sample of an IPAF patient, wherein the biomarker comprises at least one selected from the group consisting of CXCL9 and CXCL10; and treating the patient with anti-inflammatory therapy when a measured value of CXCL9 or a measured value of CXCL10 is greater than or equal to a predetermined threshold value corresponding to each biomarker.

The present invention provides a method for treating an interstitial pneumonia patient with anti-inflammatory therapy, comprising:

measuring at least one biomarker in a biological sample of the patient, wherein the biomarker is CXCL10; and identifying the patient has IPAF and treating the patient with anti-inflammatory therapy when the measured value of CXCL10 is greater than or equal to a predetermined threshold value corresponding to CXCL10.

The present invention makes it possible to acquire information on a condition of a patient with interstitial pneumonia.

BRIEF DESCRIPTION OF THE DRAWINGS

FIG. 4A is a flowchart of a determination using an apparatus for determining a condition of a patient with interstitial pneumonia;

FIG. 9 is an ROC curve when whether a patient had IPAF or IPF was determined, based on the serum CXCL10 concentration;

DETAILED DESCRIPTION OF THE PREFERRED EMBODIMENTS

Figure 1A:
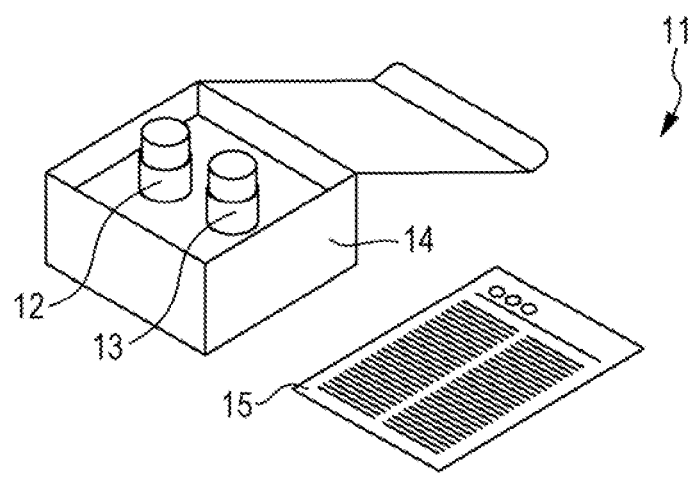
FIG. 1A is a view showing an example of an appearance of a reagent kit of the present embodiment.

[1. Method for Acquiring Information on Condition of Patient with Interstitial Pneumonia]

In the method for acquiring information on a condition of a patient with interstitial pneumonia (hereinafter, also referred to as an "acquisition method") of the present embodiment, at least one biomarker in a biological sample of an interstitial pneumonia patient is measured.

(Subject and Biological Sample)

In the present embodiment, a subject is not particularly limited as long as it is a patient diagnosed with interstitial pneumonia or a person suspected of having interstitial pneumonia. As used herein, the term "interstitial pneumonia patient" includes both a patient diagnosed with interstitial pneumonia and a person suspected of having interstitial pneumonia. The subject may be an untreated interstitial pneumonia patient. The subject may be an interstitial pneumonia patient having a collagen disease or an interstitial pneumonia patient suspected of having a collagen disease. The types of interstitial pneumonia and collagen disease are not particularly limited.

A biological sample is not particularly limited as long as it contains a biomarker described below. Examples of such a biological sample include blood samples, bronchoalveolar lavage fluids, and the like. Examples of the blood sample include blood (whole blood) collected from a subject and plasma or serum prepared from the blood. In the present embodiment, serum is particularly preferred.

When insoluble contaminants such as cells are contained in the biological sample, for example, impurities may be removed from the biological sample by a known means such as centrifugal separation and filtration. Further, the biological sample may be diluted with an appropriate aqueous medium as necessary. Such an aqueous medium is not particularly limited as long as it does not interfere with the measurement described later, and examples thereof include water, physiological saline, a buffer solution, and the like. The buffer solution is not particularly limited as long as it has a buffering effect at a pH near neutrality (for example, a pH of 6 or more and 8 or less). Examples of the buffer solution include Good buffers such as HEPES, MES, and PIPES, tris buffered saline (TBS), phosphate buffered saline (PBS), and the like.

(Biomarker and its Measurement)

The biomarker includes at least one selected from CXCL9 and CXCL10. CXCL9 is also called Monokine induced by interferon γ (MIG) and is a kind of Th1-type chemokine. CXCL10 is also called Interferon-inducible Protein-10 (IP-10) and is a kind of Th1-type chemokine, as CXCL9. CXCL9 and CXCL10 are both ligands of a CXCR3 receptor expressed on the surface of Th1 cells. The amino acid sequences of CXCL9 and CXCL10 themselves are known. For example, the amino acid sequences of CXCL9 and CXCL10 can be known from known databases such as National Center for Biotechnology Information (NCBI).

As used herein, the phrase "measuring a biomarker" includes determining the value of the amount or concentration of a biomarker and acquiring information reflecting the amount or concentration of a biomarker. The phrase "information reflecting the amount or concentration of a biomarker" means an index that changes according to the amount or concentration of a biomarker in a biological sample or a measurement sample prepared from the biological sample. Preferably, such an index is an index of optical change that is visible or mechanically measurable. Examples of the index of optical change include emission intensity, fluorescence intensity, absorbance, turbidity, density of developed color, and the like.

The information reflecting the amount or concentration of a biomarker may be qualitatively indicated, quantitatively indicated, or semi-quantitatively indicated. The information that is qualitatively indicated is information indicating the presence or absence of a biomarker. The information that is quantitatively indicated is numerical information such as a numerical value (hereinafter, also referred to as "raw data") obtained by a measuring equipment and a value calculated from the numerical value. Examples of the value calculated from the raw data include a value obtained by subtracting a value of a negative control sample or a background value from the raw data. Based on the quantitative information, the value of the amount or concentration of a biomarker can be determined. The information that is semi-quantitatively indicated is information that shows the amount or concentration of a biomarker in stages using words, numbers (indicating class), colors, and the like. For example, phrases such as "below the detection limit", "small", "medium" and "many" may be used.

In the present embodiment, the measurement result of the biomarker includes values and information obtained by measuring the biomarker, and combinations thereof. In a preferred embodiment, the measurement result of the biomarker is quantitative information reflecting the amount or concentration of the biomarker and/or a value of the amount or concentration of the biomarker determined based on the quantitative information. Hereinafter, the quantitative information reflecting the amount or concentration of the biomarker, and/or the value of the amount or concentration of the biomarker is also referred to as "the measured value of the biomarker".

The measurement result of the biomarker may be a measured value of one biomarker, or may be measured values of two biomarkers. Specifically, the measured value of the biomarker is a measured value of CXCL9 and a measured value of CXCL10. The measurement result of the biomarker may be a value calculated using measured values of two or more biomarkers. For this calculation, an arbitrary coefficient and/or constant may be further used as necessary. For example, the value calculated using the measured values of two biomarkers includes a ratio, a product, a sum and a difference between the two measured values, and the like.

The method for measuring a biomarker is not particularly limited as long as information reflecting the amount or concentration of a biomarker in a biological sample or a measurement sample prepared from the biological sample can be acquired. In the present embodiment, a method of capturing a biomarker using a substance capable of specifically binding to the biomarker is preferable. The biomarker contained in the biological sample can be measured by detecting the biomarker captured by such a substance by a method known in the art.

Examples of the substance capable of specifically binding to the biomarker include an antibody, an aptamer, a receptor protein, and the like. The antibody is particularly preferable among them. Antibodies against each of the above biomarkers themselves are known. Antibodies against each of the above biomarkers are generally available. An antibody against the biomarker is not particularly limited as long as it is an antibody capable of specifically binding to the biomarker. Such an antibody may be any of monoclonal antibodies, polyclonal antibodies, and fragments thereof (for example, Fab, F(ab')$_2$, Fab', and the like). A commercially available antibody may be used.

A method for measuring a biomarker using an antibody is not particularly limited and can be appropriately selected from known immunological measurement methods. Examples of such a measuring method include enzyme-linked immunosorbent assay (ELISA), Western blot, and the like. Among them, the ELISA is preferable. The type of the ELISA may be any of a sandwich method, a competitive method, a direct method, an indirect method and the like, and the sandwich method is particularly preferred. As an example, the case of measuring a biomarker in a biological sample by a sandwich ELISA will be described below.

First, a complex containing a biomarker, an antibody for capturing the biomarker (hereinafter also referred to as "capture antibody") and an antibody for detecting the biomarker (hereinafter also referred to as "detection antibody") is formed on a solid phase. The complex can be formed by mixing a biological sample that can contain a biomarker, a capture antibody, and a detection antibody. Then, a solution containing the complex is brought into contact with a solid phase capable of capturing the capture antibody, whereby the complex can be formed on the solid phase. Alternatively, a solid phase preliminarily immobilized with the capture antibody may be used. That is, a solid phase immobilized with the capture antibody, the biological sample, and the detection antibody are brought into contact with each other, whereby the complex can be formed on the solid phase. When both the capture antibody and the detection antibody are monoclonal antibodies, it is preferable that the epitopes be different from each other.

The solid phase may be any insoluble carrier capable of immobilizing the capture antibody. The mode of immobilization of the capture antibody on the solid phase is not particularly limited. For example, the capture antibody and the solid phase may be bound directly, or the capture antibody and the solid phase may be indirectly bound via another substance. Examples of the direct binding include physical adsorption and the like. Examples of the indirect bond include a bond via a combination of biotin and avidin or streptavidin (hereinafter also referred to as "avidins"). In this case, by preliminarily modifying the capture antibody with biotin and previously binding avidins to the solid phase, the capture antibody and the solid phase can be indirectly bound via the bond between the biotin and the avidins.

The material of the solid phase is not particularly limited, and it can be selected from, for example, organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, and the like), silica, alumina, glass, and the like. Examples of the biopolymer include insoluble agarose, insoluble dextran, gelatin, cellulose, and the like. Two or more of these may be used in combination. The shape of the solid phase is not particularly limited, and examples thereof include particles, membranes, microplates, microtubes, test tubes, and the like. Among them, particles are preferable, and magnetic particles are particularly preferable.

In the present embodiment, B/F (Bound/Free) separation for removing an unreacted free component not forming a complex may be performed between the process of forming the complex and the process of detecting the complex. The unreacted free component refers to a component not constituting a complex. Examples thereof include capture antibodies not bound to the biomarker, detection antibodies, and the like. The means of B/F separation is not particularly limited, and when the solid phase is a particle, B/F separation can be performed by recovering only the solid phase capturing the complex by centrifugation. When the solid phase is a container such as a microplate or a microtube, B/F separation can be performed by removing a liquid containing an unreacted free component. When the solid phase is a magnetic particle, B/F separation can be performed by aspirating and removing a liquid containing an unreacted free component by a nozzle while magnetically constraining the magnetic particles with a magnet, which is preferable from the viewpoint of automation. After removing the unreacted free component, the solid phase capturing the complex may be washed with a suitable aqueous medium such as PBS.

Moreover, a biomarker contained in the biological sample can be measured by detecting the complex formed on the solid phase by a method known in the art. For example, when an antibody labeled with a labeling substance is used as a detection antibody, the biomarker in the biological sample can be measured by detecting a signal generated by the labeling substance. Alternatively, also when a labeled secondary antibody against the detection antibody is used, the biomarker in the biological sample can be measured in the same manner.

As an example of a method for measuring a biomarker using an antibody, the immune complex transfer method described in JP H01-254868 A can be also used.

As used herein, the phrase "detecting a signal" includes qualitatively detecting the presence or absence of a signal, quantifying a signal intensity, and semi-quantitatively detecting the intensity of a signal. Semi-quantitative detection means to show the intensity of the signal in stages like "no signal generated", "weak", "medium", "strong", and the like. In the present embodiment, it is preferable to detect the intensity of a signal quantitatively or semi-quantitatively.

The labeling substance is not particularly limited as long as a detectable signal is generated. For example, it may be a substance which itself generates a signal (hereinafter also referred to as "signal generating substance") or a substance which catalyzes the reaction of other substances to generate a signal. Examples of the signal generating substance include fluorescent substances, radioactive isotopes, and the like. Examples of the substance that catalyzes the reaction of other substances to generate a detectable signal include enzymes. Examples of the enzymes include alkaline phosphatase, peroxidase, β-galactosidase, luciferase, and the like. Examples of the fluorescent substance include fluorescent dyes such as fluorescein isothiocyanate (FITC), rhodamine and Alexa Fluor (registered trademark), fluorescent proteins such as GFP, and the like. Examples of the radioactive isotopes include $^{125}$I, $^{14}$C, $^{32}$P, and the like. Among them, an enzyme is preferable as a labeling substance, and alkaline phosphatase and peroxidase are particularly preferable.

Methods for detecting a signal themselves are known in the art. In the present embodiment, a measurement method according to the type of signal derived from the labeling substance may be appropriately selected. For example, when the labeling substance is an enzyme, signals such as light and color generated by reacting a substrate for the enzyme can be measured by using a known apparatus such as a spectrophotometer.

The substrate of the enzyme can be appropriately selected from known substrates according to the type of the enzyme. For example, when alkaline phosphatase is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.1³,⁷]decan]-4-yl)phenyl phosphate) and CSPD (registered trademark) (disodium 3-(4-methoxyspiro[1,2-dioxetane-3,2-(5'-chloro)tricyclo[3.3.1.1³,⁷]decan]-4-yl)phenyl phosphate), and chromogenic substrates such as 5-bromo-4-chloro-3-indolyl phosphate (BCIP), disodium 5-bromo-6-chloro-indolyl phosphate, and p-nitrophenyl phosphate. When peroxidase is used as the enzyme, examples of the substrate include chemiluminescent substrates such as luminol and derivatives thereof, and chromogenic substrates such as 2,2'-azinobis(3-ethylbenzothiazoline-6-ammonium sulfonate) (ABTS), 1,2-phenylenediamine (OPD) and 3,3',5,5'-tetramethylbenzidine (TMB).

When the labeling substance is a radioactive isotope, radiation as a signal can be measured using a known apparatus such as a scintillation counter. When the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

The detection result of the signal can be used as the measurement result of the biomarker. For example, when quantitatively detecting the intensity of a signal, a measured value of the signal intensity itself or a value acquired from the measured value can be used as the measurement result of the biomarker. Examples of the value acquired from the measured value of the signal intensity include a value obtained by subtracting the measured value of a negative control sample or the background value from the measured value, and the like. The measured value of the signal intensity may be applied to a calibration curve to determine the amount or concentration value of the biomarker. The negative control sample can be appropriately selected, and examples thereof include a biological sample obtained from a healthy subject and the like.

In the present embodiment, it is preferable to measure a free protein marker contained in the biological sample by a sandwich ELISA using a capture antibody immobilized on magnetic particles and a detection antibody labeled with a labeling substance. In this case, measurement may be carried out using a commercially available fully automated immunoassay system such as HISCL series (manufactured by Sysmex Corporation).

(Information on Condition of Patient with Interstitial Pneumonia)

In the present embodiment, the measurement result of the biomarker serves as an index for discrimination between IPAF and CTD-ILD. For example, as shown in Examples, the concentrations of CXCL9 and CXCL10 in a biological sample are significantly lower in a patient group diagnosed with IPAF than in a patient group diagnosed with CTD-ILD. Therefore, in the present embodiment, the measurement result of the biomarker can be acquired as information on a condition of a patient with interstitial pneumonia. Examples of the information on a condition of a patient with interstitial pneumonia include information suggesting that the interstitial pneumonia patient has IPAF or information suggesting that the interstitial pneumonia patient has CTD-ILD. For example, when the measured value of CXCL9 or the measured value of CXCL10 is lower than a predetermined threshold value corresponding to each biomarker, the measured value may suggest that the patient has IPAF. Alternatively, when the measured value of CXCL9 or the measured value of CXCL10 is greater than or equal to the predetermined threshold value corresponding to each biomarker, the measured value may suggest that the patient has CTD-ILD. More specific embodiments are as follows.

In one embodiment, the measurement result of the biomarker is a measured value of CXCL9. In this embodiment, when the measured value of CXCL9 is lower than a predetermined threshold value corresponding to CXCL9, the measured value may suggest that the patient has IPAF. When the measured value of CXCL9 is greater than or equal to the predetermined threshold value corresponding to CXCL9, the measured value may suggest that the patient has CTD-ILD. The predetermined threshold value corresponding to CXCL9 is a threshold value for discriminating between IPAF and CTD-ILD.

In another embodiment, the measurement result of the biomarker is a measured value of CXCL10. In this embodiment, when the measured value of CXCL10 is lower than a predetermined threshold value corresponding to CXCL10, the measured value may suggest that the patient has IPAF. When the measured value of CXCL10 is greater than or equal to the predetermined threshold value corresponding to CXCL10, the measured value may suggest that the patient has CTD-ILD. The predetermined threshold value corresponding to CXCL10 is a threshold value for discriminating between IPAF and CTD-ILD.

In a further embodiment, the measurement result of the biomarker is the measured value of CXCL9 and the measured value of CXCL10. In this embodiment, when the measured value of CXCL9 is lower than a first threshold value or the measured value of CXCL10 is lower than a second threshold value, these measured values may suggest that the patient has IPAF. When the measured value of CXCL9 is greater than or equal to the first threshold value and the measured value of CXCL10 is greater than or equal to the second threshold value, these measured values may suggest that the patient has CTD-ILD. Alternatively, when the measured value of CXCL9 is lower than the first threshold value and the measured value of CXCL10 is lower than the second threshold value, these measured values may suggest that the patient has IPAF. When the measured value of CXCL9 is greater than or equal to the first threshold value or the measured value of CXCL10 is greater than or equal to the second threshold value, these measured values may suggest that the patient has CTD-ILD. The first threshold value is the predetermined threshold value corresponding to CXCL9, and the second threshold value is the predetermined threshold value corresponding to CXCL10. The first and second threshold values are threshold values for discriminating between IPAF and CTD-ILD.

In a further embodiment, the measurement result of the biomarker is also an index for discrimination between IPAF and IPF. As shown in the Examples, the concentration of CXCL10 in a biological sample is significantly lower in a patient group diagnosed with IPF than in a patient group diagnosed with IPAF. Therefore, the information on a condition of a patient with interstitial pneumonia may be information suggesting that the interstitial pneumonia patient has IPF. In this embodiment, the measurement result of the biomarker is a measured value of CXCL10. When the measured value of CXCL10 is lower than the predetermined threshold value corresponding to CXCL10, the measured value may suggest that the patient has IPF. When the measured value of CXCL10 is greater than or equal to the predetermined threshold value corresponding to CXCL10, the measured value may suggest that the patient has IPAF. The predetermined threshold value corresponding to CXCL10 is a threshold value for discriminating between IPAF and IPF.

The predetermined threshold value is not particularly limited. The predetermined threshold value can be appropriately set. For example, a predetermined threshold value may be set empirically by accumulating data of measured values of biomarkers of interstitial pneumonia patients. For example, the threshold value for discriminating between CTD-ILD and IPAF may be set as follows. First, biological samples were collected from a plurality of patients diagnosed with CTD-ILD (CTD-ILD group) and a plurality of patients diagnosed with IPAF (IPAF group), and the biomarkers were measured to obtain measured values of biomarkers. Then, a value capable of discriminating between the CTD-ILD group and the IPAF group with the highest accuracy is obtained, and the value is set as a predetermined threshold value. The threshold value for discriminating between IPAF and IPF can also be set in the same manner by using measured values of biomarkers in biological samples collected from the IPAF group and a plurality of patients diagnosed with IPF (IPF group). In setting the threshold value, it is preferable to consider sensitivity, specificity, positive predictive value, negative predictive value, and the like.

The measurement result of the biomarker obtained by the acquisition method of the present embodiment can be used for determining a condition of a patient with interstitial pneumonia. A medical worker such as a doctor may discriminate a condition using the measurement result, or may discriminate a condition by combining the measurement result with other information. The "other information" includes physical findings, tissue or image findings, blood test results, and other medical findings.

(Embodiments Using Additional Biomarkers)

The present inventors have found that it is possible to discriminate between IPAF and IPF by measuring KL-6 (Krebs von der Lungen Nr. 6) and MMP9 (Matrix metalloproteinase 9) as additional biomarkers, and combining these measurement results with the measurement results of CXCL9 and CXCL10. Therefore, in the present embodiment, the biomarker may further include at least one selected from KL-6 and MMP9. KL-6 is a kind of sialylated sugar chain antigen. KL-6 is known as a marker for interstitial pneumonia. MMP9 is an enzyme having an activity of decomposing type IV collagen and the like. MMP9 is known as a marker associated with lung fibrosis. The amino acid sequences of KL-6 and MMP9 themselves are known. For example, the amino acid sequences of KL-6 and MMP9 can be known from known databases such as NCBI. The measurement of the biomarker is as described above.

The measurement result of the biomarker includes a measured value of at least one biomarker selected from CXCL9 and CXCL10, and a measured value of at least one biomarker selected from KL-6 and MMP9. Preferably, the measurement result of the biomarker is a value acquired based on a measured value of at least one biomarker selected from CXCL9 and CXCL10 and a measured value of at least one biomarker selected from KL-6 and MMP9. Examples of such values include values obtained by multivariate analysis using measured values of each biomarker. As the value obtained by multivariate analysis, a predicted value obtained by multiple logistic regression analysis is particularly preferable. Such a predicted value can be calculated by the following regression equation.

$$P=1/[1+\exp\{-(a_1x_1+a_2x_2+\ldots+a_nx_n+b)\}]$$

In the above regression equation, $x_1$ to $x_n$ are the measured values of each biomarker, $a_1$ to $a_n$ are regression coefficients of each biomarker, and $b$ is a constant. The regression coefficients and constants can be set as appropriate depending on the type of biomarker used. For example, the regression coefficients and constants can be set, by creating a multiple logistic model for determining between IPAF and IPF, from data of measured values of biomarkers in biological samples collected from a plurality of patients diagnosed with IPAF and a plurality of patients diagnosed with IPF. The multiple logistic model can be created using statistical analysis software such as SPSS Statistics (IBM Corporation). In the present embodiment, it is preferable to create a multiple logistic model in advance from data of measured values of biomarkers of IPAF patients and IPF patients.

In the present embodiment, the value acquired based on a measured value of at least one biomarker selected from CXCL9 and CXCL10 and a measured value of at least one biomarker selected from KL-6 and MMP9 is preferably a predicted value obtained by multiple logistic regression analysis using the measured value of CXCL9 and the measured value of KL-6, the measured value of CXCL9 and the measured value of MMP9, the measured value of CXCL10 and the measured value of KL-6, or the measured value of CXCL10 and the measured value of MMP9.

When at least one selected from CXCL9 and CXCL10 and at least one selected from KL-6 and MMP9 are measured as the biomarkers, the measurement results of the biomarkers are an index for discrimination between IPAF and IPF. Specifically, information suggesting that the interstitial pneumonia patient has IPAF, or information suggesting that the interstitial pneumonia patient has IPF can be acquired as the information on a condition of a patient with interstitial pneumonia. For example, when the measurement result of the biomarker is a predicted value obtained by multiple logistic regression analysis using a measured value of at least one biomarker selected from CXCL9 and CXCL10 and a measured value of at least one biomarker selected from KL-6 and MMP9, by comparison with the threshold value, the predicted value suggests information on a condition of a patient with interstitial pneumonia as follows. When the predicted value is greater than or equal to a predetermined threshold value, the predicted value may suggest that the patient has IPAF. Alternatively, when the predicted value is lower than the predetermined threshold value, the predicted value may suggest that the patient has IPF. The predetermined threshold value is a threshold value for discriminating between IPAF and IPF. Setting of the predetermined threshold value is as described above.

[2. Method for Determining Condition of Patient with Interstitial Pneumonia]

In the present embodiment, the measurement result of the biomarker obtained by the above method can be used for determining a condition of a patient with interstitial pneumonia. In the method for determining a condition of a patient with interstitial pneumonia (hereinafter, also referred to as a "determination method") of the present embodiment, first, at least one biomarker in a biological sample of an interstitial pneumonia patient is measured. Details of this measurement are the same as those described for the acquisition method of the present embodiment.

In the determination method of the present embodiment, the condition of a patient with interstitial pneumonia is determined, based on the measurement result of the biomarker. Specifically, whether the interstitial pneumonia patient has CTD-ILD or IPAF is determined. Details of the measurement result of the biomarker are the same as those described for the acquisition method of the present embodiment. For example, when the measurement result of the biomarker is a measured value of CXCL9 or a measured value of CXCL10, when the measured value of CXCL9 or the measured value of CXCL10 is lower than a predetermined threshold value corresponding to each biomarker, the patient is determined to have IPAF. Alternatively, when the measured value of CXCL9 or the measured value of CXCL10 is greater than or equal to the predetermined threshold value corresponding to each biomarker, the patient is determined to have CTD-ILD. Details of the predetermined threshold value corresponding to each biomarker are similar to those described for the acquisition method of the present embodiment. More specific embodiments are as follows.

In one embodiment, the measurement result of the biomarker is a measured value of CXCL9. In this embodiment, when the measured value of CXCL9 is lower than a predetermined threshold value corresponding to CXCL9, the patient is determined to have IPAF. When the measured value of CXCL9 is greater than or equal to the predetermined threshold value corresponding to CXCL9, the patient is determined to have CTD-ILD. The predetermined threshold value corresponding to CXCL9 is a threshold value for discriminating between IPAF and CTD-ILD.

In another embodiment, the measurement result of the biomarker is a measured value of CXCL10. In this embodiment, when the measured value of CXCL10 is lower than a predetermined threshold value corresponding to CXCL10, the patient is determined to have IPAF. When the measured value of CXCL10 is greater than or equal to the predetermined threshold value corresponding to CXCL10, the patient is determined to have CTD-ILD. The predetermined threshold value corresponding to CXCL10 is a threshold value for discriminating between IPAF and CTD-ILD.

In a further embodiment, the measurement result of the biomarker is the measured value of CXCL9 and the measured value of CXCL10. In this embodiment, when the measured value of CXCL9 is lower than the first threshold value or the measured value of CXCL10 is lower than the second threshold value, the patient is determined to have IPAF. When the measured value of CXCL9 is greater than or equal to the first threshold value and the measured value of CXCL10 is greater than or equal to the second threshold value, the patient is determined to have CTD-ILD. Alternatively, when the measured value of CXCL9 is lower than the first threshold value and the measured value of CXCL10 is lower than the second threshold value, the patient is determined to have IPAF. When the measured value of CXCL9 is greater than or equal to the first threshold value or the measured value of CXCL10 is greater than or equal to the second threshold value, the patient is determined to have CTD-ILD. The first threshold value is the predetermined threshold value corresponding to CXCL9, and the second threshold value is the predetermined threshold value corresponding to CXCL10. The first and second threshold values are threshold values for discriminating between IPAF and CTD-ILD.

In a further embodiment, whether the interstitial pneumonia patient has IPAF or IPF is determined, based on the measurement result of the biomarker. In this embodiment, the measurement result of the biomarker is a measured value of CXCL10. When the measured value of CXCL10 is lower than the predetermined threshold value corresponding to CXCL10, the patient is determined to have IPF. When the measured value of CXCL10 is greater than or equal to the predetermined threshold value corresponding to CXCL10, the patient is determined to have IPAF. The predetermined threshold value corresponding to CXCL10 is a threshold value for discriminating between IPAF and IPF.

In the present embodiment, the biomarker may further include at least one selected from KL-6 and MMP9. Details of the measurement result of the biomarker when measuring at least one selected from CXCL9 and CXCL10 and at least one selected from KL-6 and MMP9 is similar to those described for the acquisition method of the present embodiment. Preferably, the measurement result of the biomarker is a value acquired based on a measured value of at least one biomarker selected from CXCL9 and CXCL10 and a measured value of at least one biomarker selected from KL-6 and MMP9. Such a value is a value obtained by multivariate analysis using the measured value of each biomarker, and is preferably a predicted value obtained by multiple logistic regression analysis.

When the measurement result of the biomarker is, for example, a predicted value obtained by multiple logistic regression analysis using a measured value of at least one biomarker selected from CXCL9 and CXCL10 and a measured value of at least one biomarker selected from KL-6 and MMP9, the condition of a patient with interstitial pneumonia is determined as follows, by comparing the predicted value with the threshold value. When the predicted value is greater than or equal to a predetermined threshold value, the patient is determined to have IPAF. Alternatively, when the predicted value is lower than the predetermined threshold value, the patient is determined to have IPF. The predetermined threshold value is a threshold value for discriminating between IPAF and IPF. Setting of the predetermined threshold value is as described above.

Thus, the determination method of the present embodiment makes it possible to provide a medical worker such as a doctor with information that assists determination of condition of a patient with interstitial pneumonia. Thereby, it becomes possible to provide an appropriate treatment for the interstitial pneumonia patient according to the determined condition. For example, an antifibrotic drug is used in the treatment of IPF, but when the patient is determined to have IPAF by the determination method of the present embodiment, administration of an immunosuppressant such as a steroid may be considered.

[3. Method for Treating Interstitial Pneumonia]

The present disclosure also includes a method for treating an interstitial pneumonia patient according to a condition discriminated by the determination method of the present embodiment. Therefore, one embodiment relates to a method for treating interstitial pneumonia. The method for treating interstitial pneumonia of the present embodiment includes measuring CXCL10 in a biological sample of an interstitial pneumonia patient, determining whether the patient has IPAF or IPF, based on the measurement result of CXCL10, and administering a therapeutic agent for interstitial pneumonia to the patient according to the determined condition, and when the patient is diagnosed with IPAF, an immunosuppressant is administered to the patient, and when the patient is diagnosed with IPF, an antifibrotic drug is administered to the patient. In the determination step, when the measured value of CXCL10 is greater than or equal to the predetermined threshold value corresponding to CXCL10, the patient is determined to have IPAF. Alternatively, when the measured value of CXCL10 is lower than the predetermined threshold value corresponding to CXCL10, the patient is determined to have IPF. The predetermined threshold value is a threshold value for discriminating between IPAF and IPF.

The method for treating interstitial pneumonia of a further embodiment includes measuring at least one biomarker in a biological sample of an interstitial pneumonia patient, determining whether the patient has IPAF or IPF, based on the measurement result of the biomarker, and administering a therapeutic agent for interstitial pneumonia to the patient according to the determined condition, and when the biomarker includes at least one selected from CXCL9 and CXCL10 and at least one selected from KL-6 and MMP9, and the patient is diagnosed with IPAF, an immunosuppressant is administered to the patient, and when the patient is diagnosed with IPF, an antifibrotic drug is administered to the patient. In this embodiment, the measurement result of the biomarker is preferably a value obtained by multivariate analysis using a measured value of at least one biomarker selected from CXCL9 and CXCL10 and a measured value of at least one biomarker selected from KL-6 and MMP9. The measurement result of the biomarker is more preferably a predicted value obtained by multiple logistic regression analysis. In the determination step, when the predicted value is greater than or equal to a predetermined threshold value, the patient is determined to have IPAF. Alternatively, when the predicted value is lower than the predetermined threshold value, the patient is determined to have IPF. The predetermined threshold value is a threshold value for discriminating between IPAF and IPF.

Details of the measurement of the interstitial pneumonia patient, the biological sample and the biomarkers, and the predetermined threshold value are the same as those described for the acquisition method of the present embodiment. In the administration step, it is preferable to administer a therapeutically effective amount of an immunosuppressant or antifibrotic drug to a patient. Examples of the immunosuppressant include steroid drugs such as prednisolone and methylprednisolone, cyclophosphamide, azathioprine, cyclosporine, tacrolimus, and the like. Examples of the antifibrotic drug include pirfenidone, nintedanib, and the like. The therapeutically effective amount is appropriately determined according to treatment guidelines for interstitial pneumonia and the like.

[4. Method for Acquiring Information on Treatment Responsiveness of Patient Diagnosed with IPAF]

There are still few reports evaluating interstitial pneumonia with the diagnostic criteria of IPAF proposed by ERS and ATS. Therefore, it is not yet clear what treatment should be given to patients diagnosed with IPAF according to these diagnostic criteria. However, basically, it is considered that patients diagnosed with IPAF (hereinafter, also referred to as "IPAF patients") will be subjected to anti-inflammatory therapy using an immunosuppressant or the like. On the other hand, in the case of IPAF showing a pattern of normal interstitial pneumonia (UIP) in a morphological domain (image or tissue), similarly to the treatment of IPF, it is also considered as necessary to consider use of an antifibrotic drug without performing anti-inflammatory therapy. As shown in the Examples, in IPAF patients, a significant negative correlation was observed between serum CXCL9 concentration before treatment with anti-inflammatory therapy and one-year forced vital capacity recovery. This result suggests that IPAF patients with high serum CXCL9 concentrations have high treatment responsiveness to anti-inflammatory therapy. A similar tendency was also observed for CXCL10.

Therefore, in the present embodiment, the measurement result of at least one biomarker selected from CXCL9 and CXCL10 can be an index for discriminating treatment responsiveness of IPAF patients to anti-inflammatory therapy. In the method for acquiring information on the treatment responsiveness of an IPAF patient of the present embodiment, first, at least one biomarker selected from CXCL9 and CXCL10 in a biological sample of the IPAF patient is measured. The IPAF patient may be a patient diagnosed according to the diagnostic criteria of IPAF proposed by ERS and ATS. Alternatively, the IPAF patient may be a patient diagnosed based on the determination result of the determination method of the present embodiment.

Details of the measurement of the biological sample and the biomarker are the same as those described for the acquisition method of the present embodiment.

In the present embodiment, when the measured value of CXCL9 or the measured value of CXCL10 is greater than or equal to a predetermined threshold value corresponding to each biomarker, the measured value may suggest that the IPAF patient is responsive to anti-inflammatory therapy. Alternatively, in the present embodiment, when the measured value of CXCL9 or the measured value of CXCL10 is greater than or equal to the predetermined threshold value corresponding to each biomarker, the IPAF patient may be determined to be responsive to anti-inflammatory therapy. When the IPAF patient is suggested or determined to be responsive to anti-inflammatory therapy, the anti-inflammatory therapy is expected to have an effect on the patient. The predetermined threshold value is a threshold value for discriminating treatment responsiveness of IPAF patients to anti-inflammatory therapy. Such a threshold may be, for example, the same as the threshold value for discriminating between IPAF and IPF. Details of the setting of the threshold value are the same as those described for the acquisition method of the present embodiment. More specific embodiments are as follows.

In one embodiment, the measurement result of the biomarker is a measured value of CXCL9. In this embodiment, when the measured value of CXCL9 is greater than or equal to a predetermined threshold value corresponding to CXCL9, the measured value may suggest that the IPAF patient is responsive to anti-inflammatory therapy. Alternatively, in the present embodiment, when the measured value of CXCL9 is greater than or equal to the predetermined threshold value corresponding to CXCL9, the IPAF patient may be determined to be responsive to anti-inflammatory therapy. The predetermined threshold value corresponding to CXCL9 is a threshold value for discriminating treatment responsiveness of IPAF patients to anti-inflammatory therapy.

In another embodiment, the measurement result of the biomarker is a measured value of CXCL10. In this embodiment, when the measured value of CXCL10 is greater than or equal to a predetermined threshold value corresponding to CXCL10, the measured value may suggest that the IPAF patient is responsive to anti-inflammatory therapy. Alternatively, in the present embodiment, when the measured value of CXCL10 is greater than or equal to the predetermined threshold value corresponding to CXCL10, the IPAF patient may be determined to be responsive to anti-inflammatory therapy. The predetermined threshold value corresponding to CXCL10 is a threshold value for discriminating treatment responsiveness of IPAF patients to anti-inflammatory therapy.

In a further embodiment, the measurement result of the biomarker is the measured value of CXCL9 and the measured value of CXCL10. In this embodiment, when the measured value of CXCL9 is greater than or equal to the first threshold value and the measured value of CXCL10 is greater than or equal to the second threshold value, these measured values may suggest that the IPAF patient is responsive to anti-inflammatory therapy. Alternatively, in the present embodiment, when the measured value of CXCL9 is greater than or equal to the first threshold value and the measured value of CXCL10 is greater than or equal to the second threshold value, the IPAF patient may be determined to be responsive to anti-inflammatory therapy. When the measured value of CXCL9 is greater than or equal to the first threshold value or the measured value of CXCL10 is greater than or equal to the second threshold value, these measured values may suggest that the IPAF patient is responsive to anti-inflammatory therapy. Alternatively, in the present embodiment, when the measured value of CXCL9 is greater than or equal to the first threshold value or the measured value of CXCL10 is greater than or equal to the second threshold value, the IPAF patient may be determined to be responsive to anti-inflammatory therapy. The first threshold value is the predetermined threshold value corresponding to CXCL9, and the second threshold value is the predetermined threshold value corresponding to CXCL10. The first and second threshold values are threshold values for discriminating treatment responsiveness of IPAF patients to anti-inflammatory therapy.

[5. Reagent Kit]

The scope of the present disclosure also includes a reagent kit used for the method and determination method of the present embodiment. That is, a reagent kit including a reagent containing a substance capable of specifically binding to CXCL9 and/or a reagent containing a substance capable of specifically binding to CXCL10 (hereinafter, also referred to as "reagent kit") is provided. Details of the substances capable of specifically binding to each of CXCL9 and CXCL10 are the same as those described for the substance capable of specifically binding to the biomarker used in the method of the present embodiment.

In the present embodiment, the reagent containing a substance capable of specifically binding to CXCL9 is preferably a combination of a reagent containing a capture antibody to CXCL9 and a reagent containing a detection antibody to CXCL9. The reagent containing a substance capable of specifically binding to CXCL10 is preferably a combination of a reagent containing a capture antibody to CXCL10 and a reagent containing a detection antibody to CXCL10. The detection antibody may be labeled with a labeling substance. When the labeling substance is an enzyme, the reagent kit may include a substrate for the enzyme. Details of the capture antibody, the detection antibody, the labeling substance and the substrate are the same as those described in the method of the present embodiment. The forms of the capture antibody, the detection antibody, the labeling substance and the substrate are not particularly limited, and they may be a solid (for example, powder, crystal, freeze-dried product, and the like) or liquid (for example, solution, suspension, emulsion, and the like).

Figure 11:
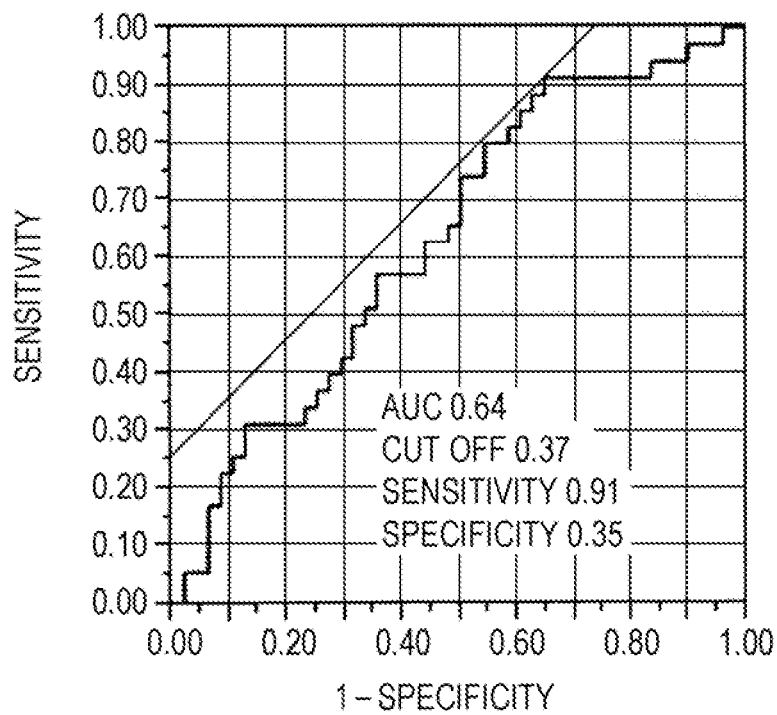
FIG. 11 is an ROC curve when whether a patient had IPAF or IPF was determined, based on a predicted value calculated from serum CXCL9 and KL-6 concentrations.
Figure 12:
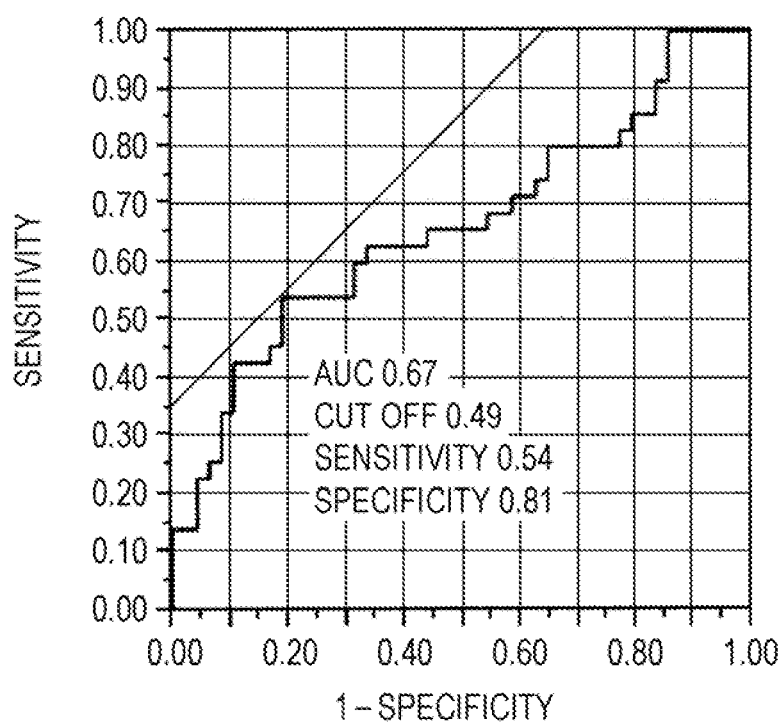
FIG. 12 is an ROC curve when whether a patient had IPAF or IPF was determined, based on a predicted value calculated from serum CXCL9 and MMP9 concentrations.
Figure 13:
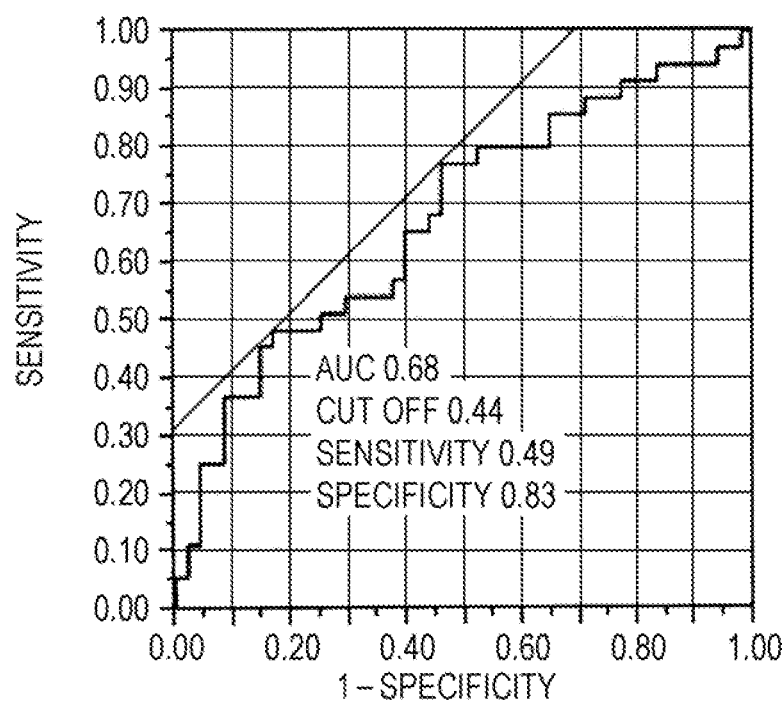
FIG. 13 is an ROC curve when whether a patient had IPAF or IPF was determined, based on a predicted value calculated from serum CXCL10 and KL-6 concentrations.
Figure 14:
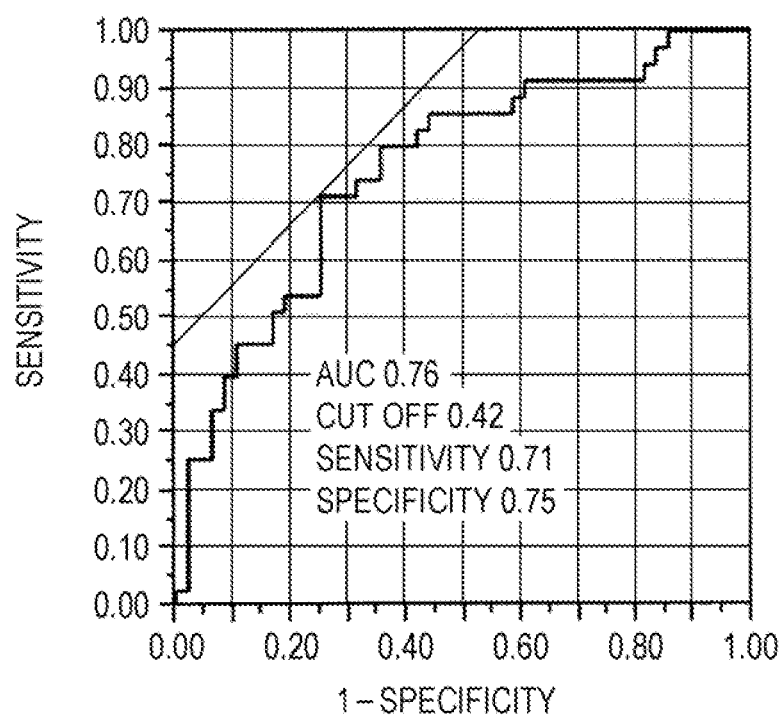
FIG. 14 is an ROC curve when whether a patient had IPAF or IPF was determined, based on a predicted value calculated from serum CXCL10 and MMP9 concentrations.

In the present embodiment, a container storing each reagent may be packed in a box and provided to the user. The box may contain an attached document. The attached document may describe a configuration of the reagent kit, method of use, relationship between the measurement results obtained by the reagent kit and the condition of a patient with interstitial pneumonia, and the like. Examples of such reagent kits are shown in the figure. The reagent kit shown in FIG. 1A includes, as a reagent containing a substance capable of specifically binding to CXCL9, a reagent containing a capture antibody to CXCL9 and a reagent containing a detection antibody to CXCL9, but the present disclosure is not limited to this example. With reference to FIG. 1A, 11 denotes a reagent kit, 12 denotes a first container storing a reagent containing a capture antibody to CXCL9, 13 denotes a second container storing a reagent containing a detection antibody to CXCL9, 14 denotes a packing box, and 15 denotes an attached document. In this example, the first container may store a reagent containing a capture antibody to CXCL10, instead of the reagent containing a capture antibody to CXCL9. The second container may store a reagent containing a detection antibody to CXCL10, instead of the reagent containing a detection antibody to CXCL9. In this example, the reagent kit may further include a solid phase for immobilizing the capture antibody on CXCL9. Details of the solid phase are similar to those described in the acquisition method of the present embodiment.

Figure 1B:
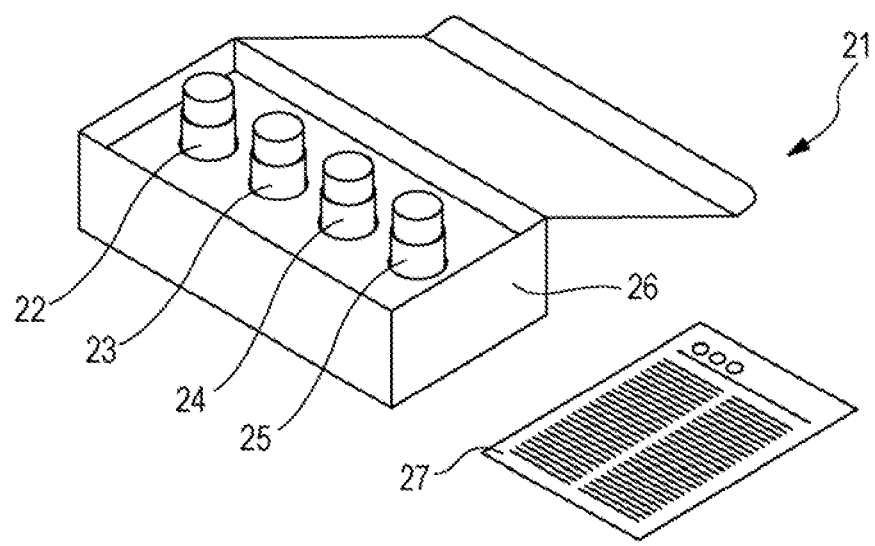
FIG. 1B is a view showing an example of an appearance of a reagent kit of the present embodiment.

The reagent kit shown in FIG. 1B further includes, as a reagent containing a substance capable of specifically binding to CXCL10, a reagent containing a capture antibody to CXCL10 and a reagent containing a detection antibody to CXCL10, but the present disclosure is not limited to this example. With reference to FIG. 1B, 21 denotes a reagent kit, 22 denotes a first container storing a reagent containing a capture antibody to CXCL9, 23 denotes a second container storing a reagent containing a detection antibody to CXCL9, 24 denotes a third container storing a reagent containing a capture antibody to CXCL10, 25 denotes a fourth container storing a reagent containing a detection antibody to CXCL10, 26 denotes a packing box, and 27 denotes an attached document. In this example, the reagent kit may further include a solid phase for immobilizing each of the capture antibody on CXCL9 and the capture antibody on CXCL10. Details of the solid phase are similar to those described in the acquisition method of the present embodiment.

The reagent kit of the present embodiment may further include at least one reagent selected from a reagent containing a substance capable of specifically binding to KL-6 and a reagent containing a substance capable of specifically binding to MMP9. The reagent containing a substance capable of specifically binding to KL-6 is preferably a combination of a reagent containing a capture antibody to KL-6 and a reagent containing a detection antibody to KL-6. The reagent containing a substance capable of specifically binding to MMP9 is preferably a combination of a reagent containing a capture antibody to MMP9 and a reagent containing a detection antibody to MMP9.

The reagent kit of the present embodiment may include a calibrator for each biomarker. Examples of the calibrator include a CXCL9 calibrator and a CXCL10 calibrator. The CXCL9 calibrator may include, for example, a buffer solution containing no CXCL9 (negative control) and a buffer solution containing a CXCL9 at a known concentration. The CXCL10 calibrator may include, for example, a buffer solution containing no CXCL10 (negative control) and a buffer solution containing a CXCL10 at a known concentration. Another example of the calibrator includes a buffer solution containing neither CXCL9 nor CXCL10 (negative control), a buffer solution containing CXCL9 at a known concentration, and a buffer solution containing CXCL10 at a known concentration. Another example of the calibrator includes a buffer solution containing neither CXCL9 nor CXCL10 (negative control), and a buffer solution containing CXCL9 and CXCL10 at known concentrations, respectively.

When the reagent kit includes at least one reagent selected from a reagent containing a substance capable of specifically binding to KL-6 and a reagent containing a substance capable of specifically binding to MMP9, the reagent kit may include calibrators of these biomarkers. Examples of the calibrator include a calibrator for quantifying KL-6 and a calibrator for quantifying MMP9. The KL-6 calibrator may include, for example, a buffer solution containing no KL-6 (negative control) and a buffer solution containing a KL-6 at a known concentration. The MMP9 calibrator may include, for example, a buffer solution containing no MMP9 (negative control) and a buffer solution containing a MMP9 at a known concentration. Another example of the calibrator includes a buffer solution containing neither KL-6 nor MMP9 (negative control), a buffer solution containing KL-6 at a known concentration, and a buffer solution containing MMP9 at a known concentration. Another example of the calibrator includes a buffer solution containing neither KL-6 nor MMP9 (negative control), a buffer solution containing KL-6 and MMP9 at known concentrations, respectively.

[6. Apparatus and Computer Program]

The scope of the present disclosure also includes an apparatus and a computer program for performing the method for determining a condition of a patient with interstitial pneumonia of the present embodiment. An example of an apparatus for determining a condition of a patient with interstitial pneumonia of the present embodiment will be described with reference to the drawings. However, the present embodiment is not limited only to the embodiment shown in this example. A determination apparatus 10 shown in FIG. 2 includes a measuring device 20, a computer system 30, and a printer 40. The measuring device 20 and the printer 40 are connected to the computer system 30.

The type of measuring device is not particularly limited, and it can be appropriately selected according to the method for measuring a biomarker. In the example shown in FIG. 2, the measuring device 20 is a commercially available automated immunoassay system capable of detecting a chemiluminescent signal generated by a sandwich ELISA using magnetic particles on which a capture antibody is immobilized and an enzyme-labeled detection antibody. However, the present disclosure is not limited to this example. When the biomarker is measured by the ELISA, the measuring device is not particularly limited as long as it can detect a signal based on the used labeling substance.

When a reagent containing magnetic particles on which a capture antibody is immobilized, a reagent containing an enzyme-labeled detection antibody and a biological sample collected from an interstitial pneumonia patient are set in the measuring device 20, the measuring device 20 performs an antigen-antibody reaction using each reagent, the measuring device 20 acquires a chemiluminescent signal as optical information based on the enzyme-labeled antibody specifically bound to a biomarker, and the measuring device 20 transmits the acquired optical information to the computer system 30.

Figure 2:
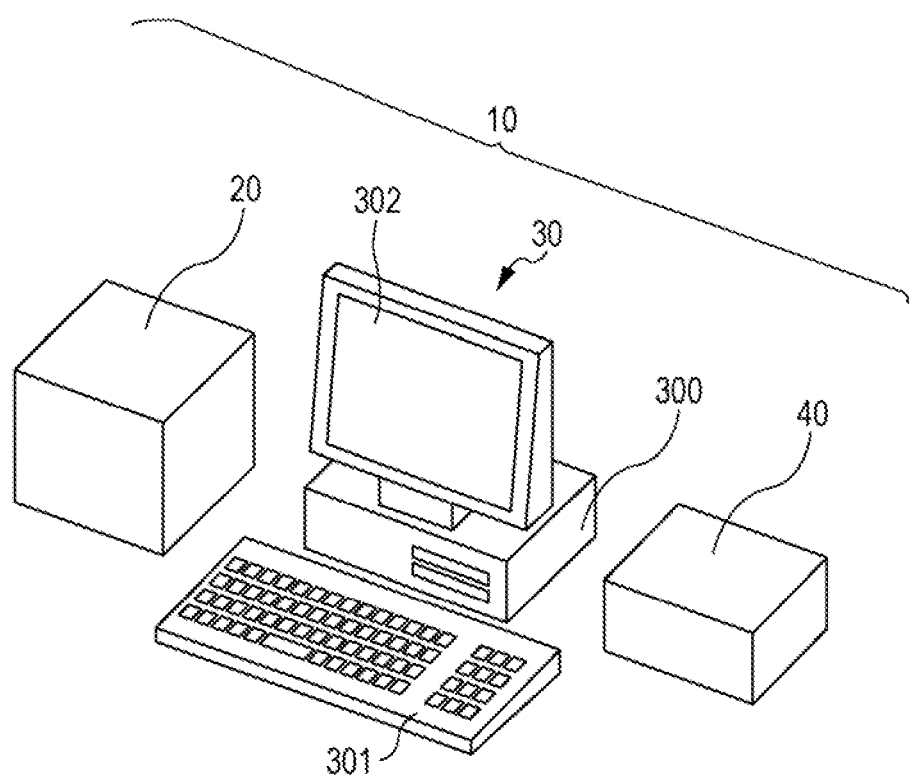
FIG. 2 is a schematic diagram showing an example of an apparatus for determining a condition of a patient with interstitial pneumonia.

The computer system 30 includes a computer main body 300, an input unit 301, and a display unit 302. The display unit 302 displays specimen information, determination results, and the like. The computer system 30 receives the optical information from the measuring device 20. Then, a processor of the computer system 30 executes a computer program for determining a condition of a patient with interstitial pneumonia, installed in a hard disk 313, based on the optical information. As shown in FIG. 2, the computer system 30 may be equipment separate from the measuring device 20. Alternatively, the computer system 30 may be equipment including the measuring device 20. In the latter case, the computer system 30 may itself be the determination apparatus 10. A commercially available automated immunoassay system may be loaded with the computer program for determining a condition of a patient with interstitial pneumonia.

Figure 3:
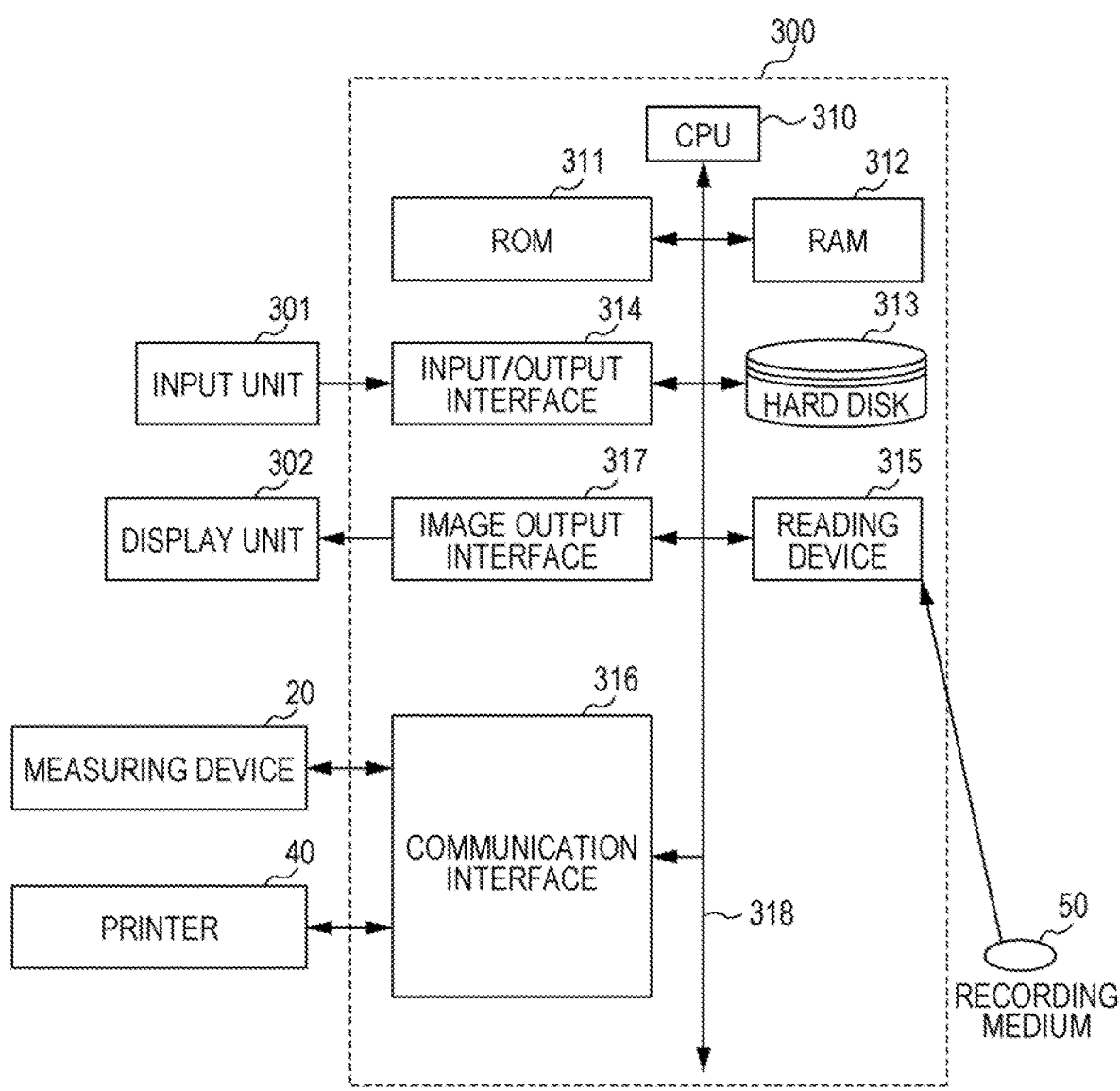
FIG. 3 is a block diagram showing a hardware configuration of an apparatus for determining a condition of a patient with interstitial pneumonia.

With reference to FIG. 3, the computer main body 300 includes a central processing unit (CPU) 310, a read only memory (ROM) 311, a random access memory (RAM) 312, a hard disk 313, an input/output interface 314, a reading device 315, a communication interface 316, and an image output interface 317. The CPU 310, the ROM 311, the RAM 312, the hard disk 313, the input/output interface 314, the reading device 315, the communication interface 316 and the image output interface 317 are data-communicably connected by a bus 318. The measuring device 20 and the printer 40 are communicably connected to the computer system 30 via the communication interface 316.

The CPU 310 can execute a program stored in the ROM 311 or the hard disk 313 and a program loaded in the RAM 312. The CPU 310 acquires a measured value of the biomarker, based on the optical information acquired from the measuring device 20. When at least one selected from CXCL9 and CXCL10 and at least one selected from KL-6 and MMP9 are measured, the CPU 310 may acquire a value obtained from the measured values of these biomarkers, for example, a predicted value obtained by multiple logistic regression analysis. Details of these values are the same as those described for the acquisition method of the present embodiment. The CPU 310 determines a condition of interstitial pneumonia based on the acquired value and a predetermined threshold value stored in the ROM 311 or the hard disk 313. The CPU 310 outputs the determination result. The CPU 310 displays the determination result on the display unit 302. The threshold value corresponding to each biomarker may be stored in advance in the ROM 311 or the hard disk 313 by a manufacturer when the computer system is manufactured. Alternatively, the user may input a threshold value corresponding to each biomarker using the input unit 301 to store the threshold value in the ROM 311 or the hard disk 313.

The ROM 311 includes a mask ROM, PROM, EPROM, EEPROM, and the like. In the ROM 311, a computer program executed by the CPU 310 and data used for executing the computer program are recorded. In the ROM 411, data used for a determination flow to be described later such as the predetermined threshold value corresponding to each biomarker and the above regression equation may be recorded.

The RAM 312 includes SRAM, DRAM, and the like. The RAM 312 is used for reading the program recorded in the ROM 311 and the hard disk 313. The RAM 312 is used as a work area of the CPU 310 when these programs are executed.

The hard disk 313 has installed therein an operating system to be executed by the CPU 310, a computer program such as an application program (program for determining a condition of a patient with interstitial pneumonia), and data used for executing the computer program. In the hard disk 313, data used for a determination flow to be described later such as the predetermined threshold value corresponding to each biomarker and the above regression equation may be recorded.

The reading device 315 includes a flexible disk drive, a CD-ROM drive, a DVD-ROM drive, a USB port, an SD card reader, a CF card reader, a memory stick reader, a solid state drive, and the like. The reading device 315 can read a program or data recorded on a portable recording medium 50.

The input/output interface 314 includes, for example, a serial interface such as USB, IEEE1394 and RS-232C, a parallel interface such as SCSI, IDE and IEEE1284, and an analog interface including a D/A converter, an A/D converter and the like. The input unit 301 such as a keyboard and a mouse is connected to the input/output interface 314. The user can input various commands to the computer main body 300 through the input unit 301.

The communication interface 316 is, for example, a wireless interface conforming to a standard such as an Ethernet (registered trademark), IEEE802.11 series or Bluetooth (registered trademark). The computer main body 300 can transmit print data to the printer 40 or the like through the communication interface 316. The printer 40 is, for example, a laser printer, an inkjet printer, or the like. When the communication interface 316 is a wireless interface, the computer main body 300 can transmit data to a mobile device such as a mobile phone or a tablet terminal.

The image output interface 317 is connected to the display unit 302 including an LCD, a CRT, and the like. As a result, the display unit 302 can output a video signal corresponding to the image data coming from the CPU 310. The display unit 302 displays an image (screen) according to the input video signal.

With reference to FIG. 4A, a determination flow of a condition of a patient with interstitial pneumonia executed by the determination apparatus 10 will be described. Here, a case will be described as an example in which a measured value of CXCL9 is acquired from the intensity of the chemiluminescent signal generated by the sandwich ELISA, and the acquired measured value and a predetermined threshold value corresponding to CXCL9 are used to determine whether the patient has IPAF or CTD-ILD. However, the present embodiment is not limited to this example. Instead of the measured value of CXCL9, the measured value of CXCL10 may be acquired.

In step S101, the CPU 310 acquires optical information (chemiluminescent signal) from the measuring device 20, and the CPU 310 stores the optical information in the hard disk 313. In step S102, the CPU 310 acquires the measured value of CXCL9 from the acquired optical information, and the CPU 310 stores the measured value of CXCL9 in the hard disk 313. In step S103, the CPU 310 compares the acquired measured value with the predetermined threshold value stored in the hard disk 313. When the measured value is lower than the predetermined threshold value, the process proceeds to step S104. In step S104, the CPU 310 stores a determination result indicating that the patient has IPAF in the hard disk 313. When the measured value is greater than or equal to the predetermined threshold value, the process proceeds to step S105. In step S105, the CPU 310 stores a determination result indicating that the patient has CTD-ILD in the hard disk 313. In step S106, the CPU 310 outputs the determination result. For example, the CPU 310 displays the determination result on the display unit 302, the CPU 310 prints the determination result with the printer 40, or the CPU 310 transmits the determination result to a mobile device such as a mobile phone or a tablet terminal. Accordingly, it is possible to provide doctors and the like with information to assist the determination of a condition of a patient with interstitial pneumonia.

Figure 4B:
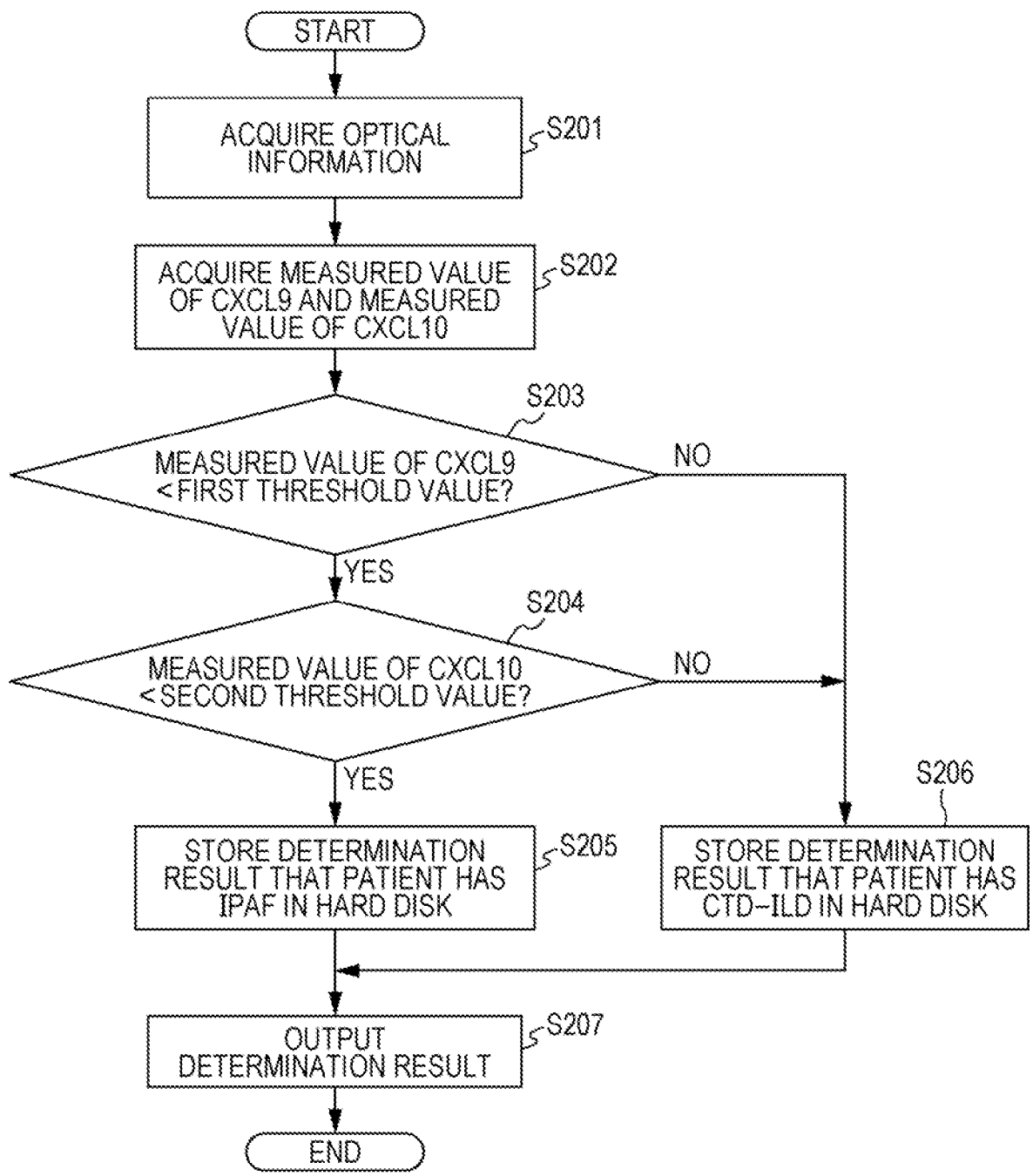
FIG. 4B is a flowchart of a determination using an apparatus for determining a condition of a patient with interstitial pneumonia.

With reference to FIG. 4B, a case will be described as an example in which a measured value of CXCL9 and a measured value of CXCL10 are acquired, and determination is made using these measured values and a predetermined threshold value corresponding to each biomarker are used to make determination. In this example, the first threshold value is the predetermined threshold value corresponding to CXCL9, and the second threshold value is the predetermined threshold value corresponding to CXCL10. Details of steps S201 and S207 are similar to those described for the steps S101 and S106, respectively. In step S202, the CPU 310 acquires the measured values of CXCL9 and CXCL10 from the acquired optical information, and the CPU 310 stores the measured values in the hard disk 313. In step S203, the CPU 310 compares the acquired measured value of CXCL9 with the first threshold value stored in the hard disk 313. When the measured value of CXCL9 is lower than the first threshold value, the process proceeds to step S204. In step S204, the CPU 310 compares the acquired measured value of CXCL10 with the second threshold value stored in the hard disk 313. When the measured value of CXCL10 is lower than the second threshold value, the process proceeds to step S205. In step S205, the CPU 310 stores a determination result indicating that the patient has IPAF in the hard disk 313.

When the measured value of CXCL9 is greater than or equal to the first threshold value in step S203, the process proceeds to step S206. When the measured value of CXCL10 is greater than or equal to the second threshold value in step S204, the process proceeds to step S206. In step S206, the CPU 310 stores a determination result indicating that the patient has CTD-ILD in the hard disk 313. In this example, the order of processes of steps S203 and S204 can be changed.

Figure 4C:
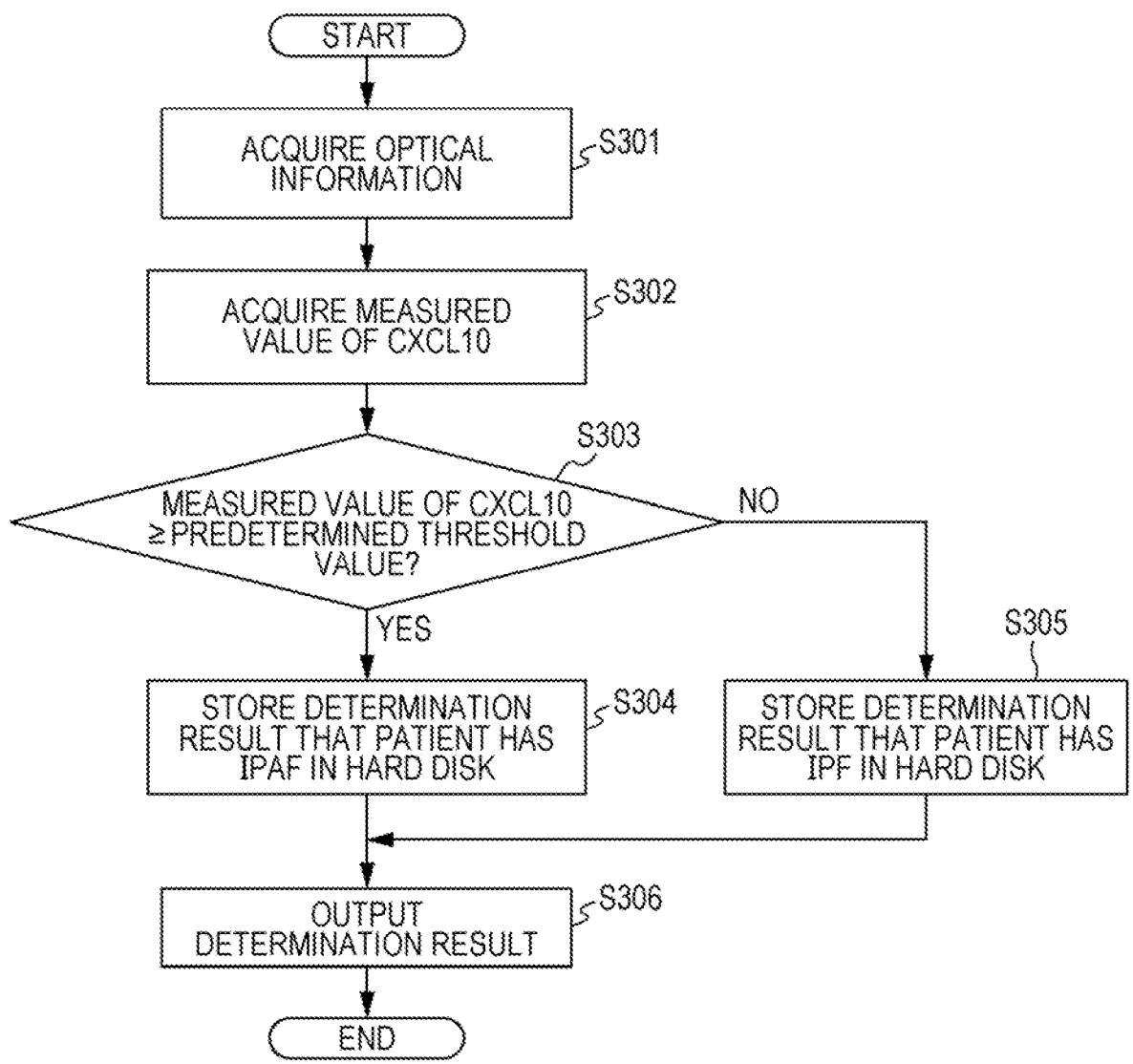
FIG. 4C is a flowchart of a determination using an apparatus for determining a condition of a patient with interstitial pneumonia.

With reference to FIG. 4C, a case will be described as an example in which a measured value of CXCL10 is acquired, and the acquired measured value and a predetermined threshold value corresponding to CXCL10 are used to determine whether the patient has IPAF or IPF. Details of steps S301 and S306 are similar to those described for the steps S101 and S106, respectively. In step S302, the CPU 310 acquires the measured value of CXCL10 from the acquired optical information, and the CPU 310 stores the measured value of CXCL10 in the hard disk 313. In step S303, the CPU 310 compares the acquired measured value with the predetermined threshold value stored in the hard disk 313. When the measured value is greater than or equal to the predetermined threshold value, the process proceeds to step S304. In step S304, the CPU 310 stores a determination result indicating that the patient has IPAF in the hard disk 313. When the measured value is lower than the predetermined threshold value, the process proceeds to step S305. In step S305, the CPU 310 stores a determination result indicating that the patient has IPF in the hard disk 313.

Figure 4D:
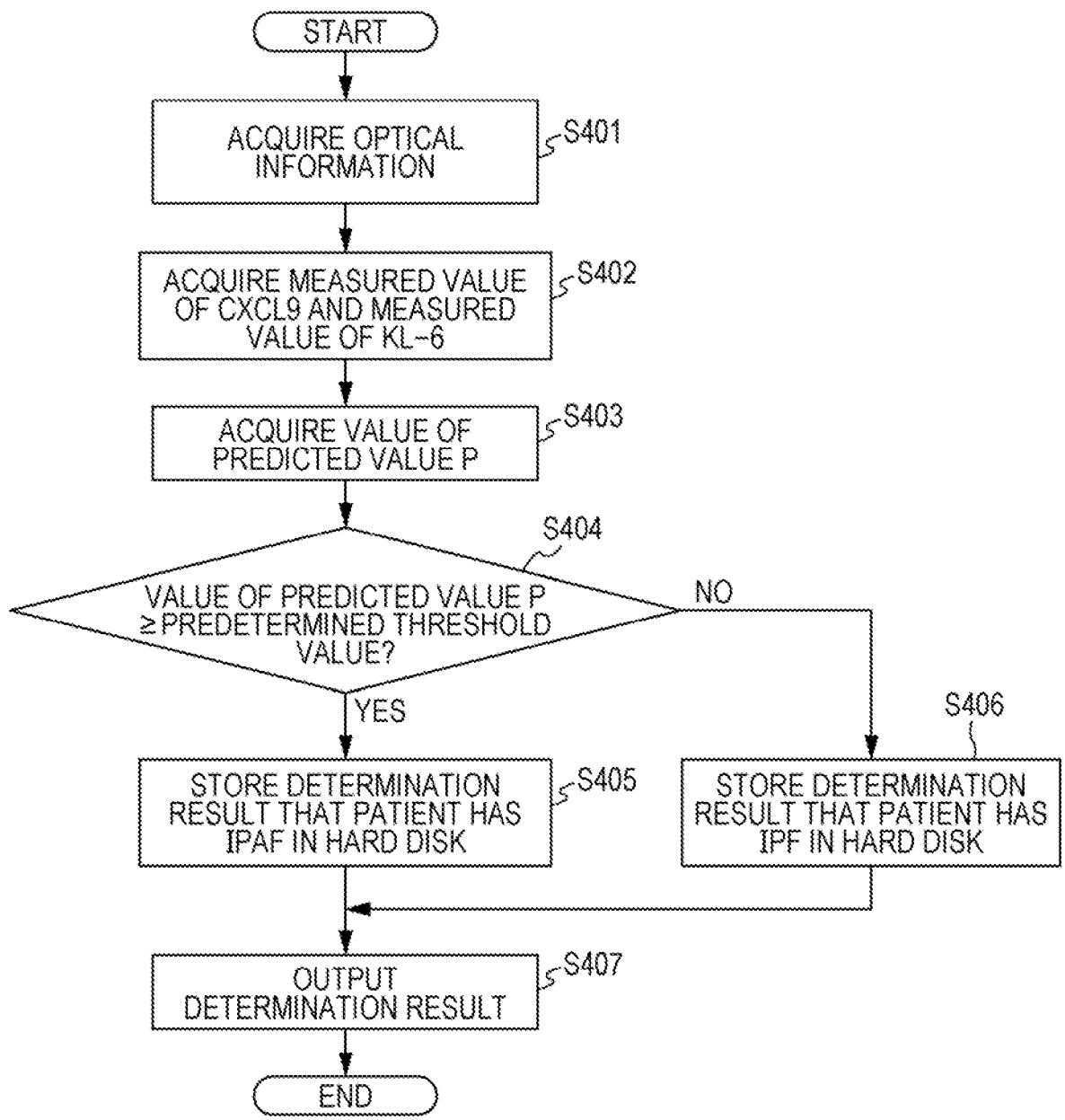
FIG. 4D is a flowchart of a determination using an apparatus for determining a condition of a patient with interstitial pneumonia.

With reference to FIG. 4D, a case will be described as an example in which a measured value of CXCL9 and a measured value of KL-6 are acquired, a predicted value P is calculated by the above regression equation using these measured values, and the predicted value P and a predetermined threshold value are used to make determination. However, the present embodiment is not limited to this example. Instead of the measured value of CXCL9, the measured value of CXCL10 may be acquired. Instead of the measured value of KL-6, the measured value of MMP9 may be acquired. Details of steps S401 and S407 are similar to those described for the steps S101 and S106, respectively. In step S402, the CPU 310 acquires the measured values of CXCL9 and KL-6 from the acquired optical information, and the CPU 310 stores the measured values in the hard disk 313. In step S403, the CPU 310 calculates a predicted value P based on the multiple logistic model according to the regression equation stored in the hard disk 313, and the CPU 310 stores the predicted value P in the hard disk 313. In step S404, the CPU 310 compares the calculated predicted value P with the predetermined threshold value stored in the hard disk 313. When the predicted value P is greater than or equal to the predetermined threshold value, the process proceeds to step S405. In step S405, the CPU 310 stores a determination result indicating that the patient has IPAF in the hard disk 313. When the predicted value P is lower than the predetermined threshold value, the process proceeds to step S406. In step S406, the CPU 310 stores a determination result indicating that the patient has IPF in the hard disk 313.

Hereinbelow, the present invention will be described in detail by examples, but the present invention is not limited to these examples. Hereinafter, "HISCL" is a registered trademark of Sysmex Corporation.

EXAMPLES

Example 1

(1) Biological Sample

Sera of 102 patients with interstitial pneumonia were used as biological samples. Of the 102 patients, 16 patients were diagnosed with CTD-ILD (CTD-ILD group), 35 patients were diagnosed with IPAF (IPAF group), and 51 patients were diagnosed with IPF (IPF group).

(2) Measurement of Biomarkers (2.1) Measurement of CXCL9

The serum CXCL9 concentration of each patient was measured using a fully automated immunoassay system HISCL-5000 or HISCL-2000i (Sysmex Corporation) using following R1 to R5 reagents.

R1 Reagent

An anti-MIG monoclonal antibody (Randox Laboratories Ltd.) was digested with pepsin or IdeS protease by a conventional method to obtain a Fab fragment. The Fab fragment was labeled with biotin by a conventional method and dissolved in a buffer containing 1% bovine serum albumin (BSA) and 0.5% casein to obtain an R1 reagent.

R2 Reagent

Magnetic particles on which streptavidin was immobilized on its surface (hereinafter also referred to as "STA-bound magnetic particles". average particle size: 2 µm; the amount of streptavidin per 1 g of the magnetic particles is 2.9 to 3.5 mg) was washed 3 times with a 10 mM HEPES buffer solution (pH 7.5). The washed STA-bound magnetic particles were added to a 10 mM HEPES (pH 7.5) so as to have a streptavidin concentration of 18 to 22 µg/ml (a concentration of STA-bound magnetic particles of 0.48 to 0.52 mg/ml) to obtain an R2 reagent.

R3 Reagent

An anti-MIG monoclonal antibody (Randox Laboratories Ltd.) was digested with pepsin or IdeS protease by a conventional method to obtain a Fab fragment. The Fab fragment was labeled with alkaline phosphatase (ALP) by a conventional method and dissolved in a buffer containing 1% BSA and 0.5% casein to obtain an R3 reagent.

R4 reagent and R5 Reagent

HISCL R4 reagent (Sysmex Corporation) as a measurement buffer solution was used as an R4 reagent. HISCL R5 reagent (Sysmex Corporation) containing CDP-Star (registered trademark) (Applied Biosystems) as a chemiluminescent substrate of ALP was used as an R5 reagent.

The measurement procedure using HISCL-5000 or HISCL-2000i was as follows. After mixing serum (20 µL) and the R1 reagent (50 µL), the R2 reagent (30 µL) was added thereto. The magnetic particles in the obtained mixed solution were magnetically collected to remove the supernatant, and a HISCL washing solution (300 µL) was added to wash the magnetic particles. The supernatant was removed, and the R3 reagent (100 µL) was added to the magnetic particles and mixed. The magnetic particles in the obtained mixed solution were magnetically collected to remove the supernatant, and a HISCL washing solution (300 µL) was added to wash the magnetic particles. The supernatant was removed, and the R4 reagent (50 µL) and the R5 reagent (100 µL) were added to the magnetic particles, and the chemiluminescence intensity was measured. The obtained chemiluminescence intensity was applied to a calibration curve to determine the concentration of CXCL9.

(2.2) Measurement of CXCL10

The serum CXCL10 concentration of each patient was measured by enzyme-linked immunosorbent assay (ELISA). The measurement procedure of CXCL10 was as follows. An anti-CXCL10 mouse monoclonal antibody sensitized to a 96-well plate at 2 µg/mL was reacted with serum (100 µL) diluted 5-fold with a specimen diluent for 2 hours. After washing 6 times with a HISCL washing solution (300 µL), 100 µL of a biotinylated goat anti-human CXCL10 antibody (0.0125 µg/mL, 1% BSA 0.5% casein PBS pH 7.4) was added thereto, and the mixture was reacted for 2 hours. After washing 6 times with a HISCL washing solution (300 µL), 100 µL of streptavidin ALP was added thereto, and the mixture was reacted for 20 minutes. After washing 6 times with a HISCL washing solution (300 µL), 100 µL of the R4 and R5 reagents mixed at 1:2 were added thereto, and the luminescent signal was counted using a plate reader. R & D Systems Duoset DY266 was used as the anti-CXCL10 antibody.

(3) Measurement Results

Figure 5:
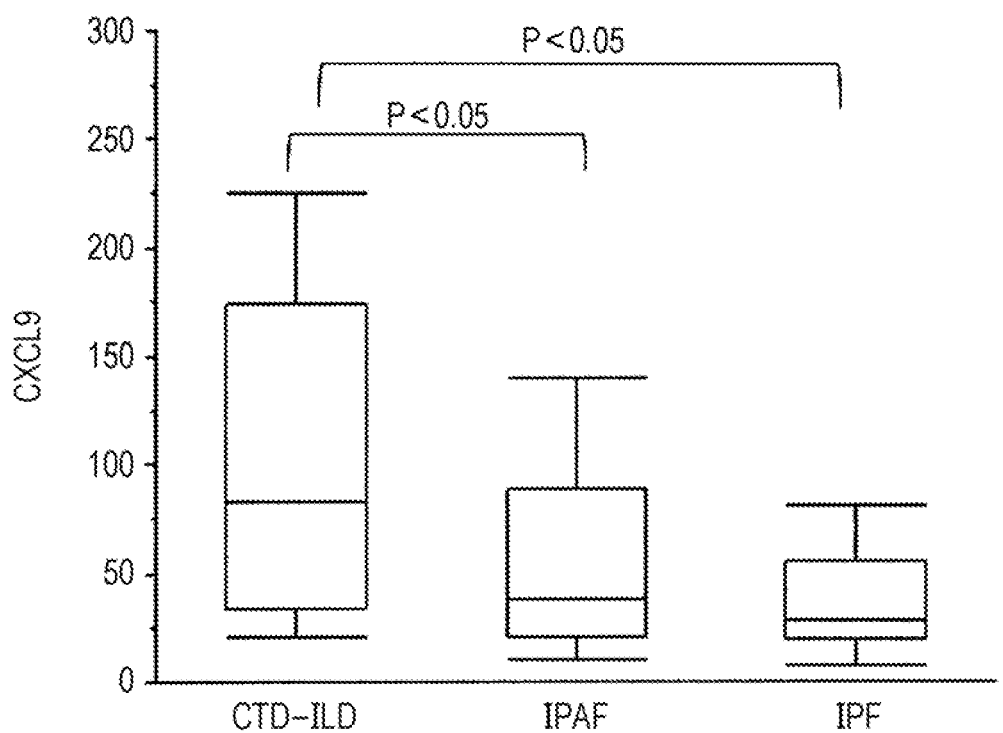
FIG. 5 is a graph showing serum CXCL9 concentrations in each patient group of CTD-ILD, IPAF and IPF.
Figure 6:
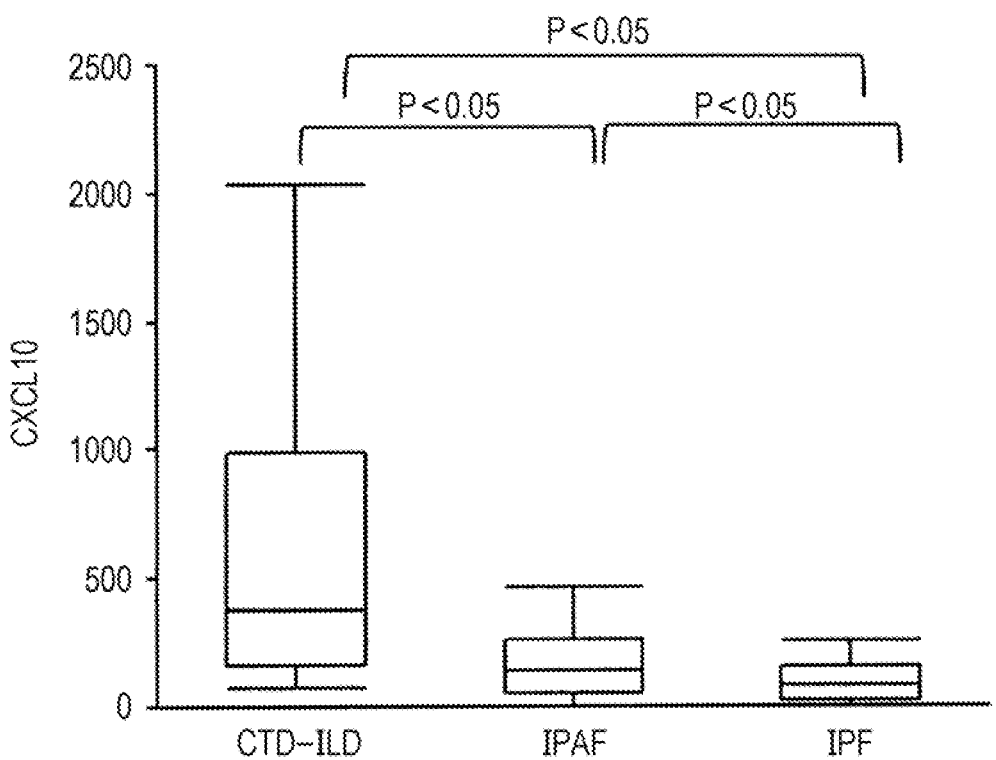
FIG. 6 is a graph showing serum CXCL10 concentrations in each patient group of CTD-ILD, IPAF and IPF.

The serum CXCL9 and CXCL10 concentrations in each patient group of CTD-ILD, IPAF and IPF are shown in FIGS. 5 and 6, respectively. It was found that the concentrations of CXCL9 and CXCL10 were significantly lower in the IPAF and IPF groups than in the CTD-ILD group. Therefore, it was suggested that serum CXCL9 and CXCL10 can be used as a biomarker that enables discrimination between CTD-ILD and IPAF. In addition, it was found that the concentration of CXCL10 was significantly lower in the IPF group than in the IPAF group. This suggested that the serum CXCL10 can be used as a biomarker also capable of discriminating between IPAF and IPF.

Example 2

(1) Discrimination Between CTD-ILD and IPAF

Figure 7:
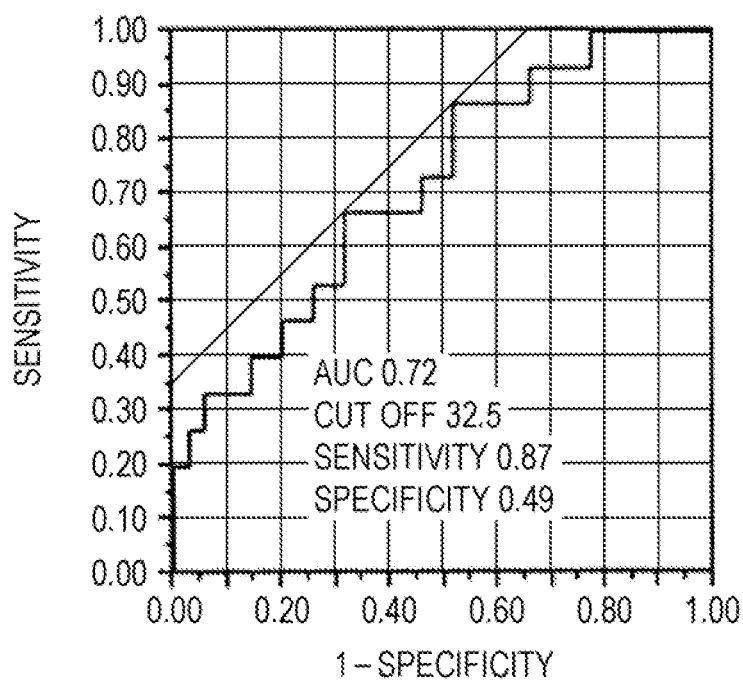
FIG. 7 is a receiver operating characteristic (ROC) curve when whether a patient had CTD-ILD or IPAF was determined, based on the serum CXCL9 concentration.
Figure 8:
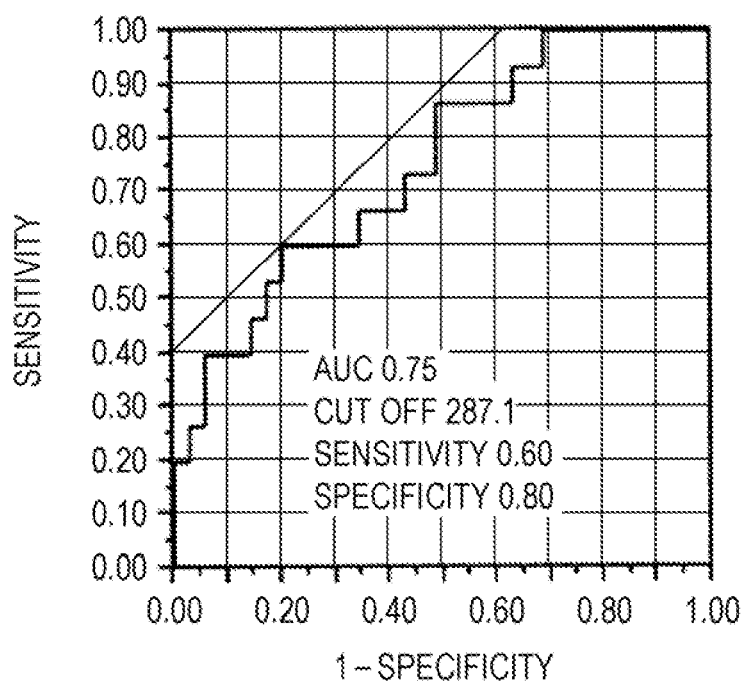
FIG. 8 is an ROC curve when whether a patient had CTD-ILD or IPAF was determined, based on the serum CXCL10 concentration.

For each concentration of CXCL9 and CXCL10 in the serum, an optimal cut-off value for distinguishing between the CTD-ILD group (16 patients) and the IPAF group (35 patients) in Example 1 was determined by ROC analysis. The sensitivity, specificity and area under the curve (AUC) for determination using the set cut-off value were calculated. In this determination, when the concentration of CXCL9 or CXCL10 was greater than or equal to the cut-off value, the patient was determined to have CTD-ILD. When the concentration of CXCL9 or CXCL10 was lower than the cut-off value, the patient was determined not to have CTD-ILD. The obtained ROC curves are shown in FIGS. 7 and 8. Table 1 shows the cut-off value (pg/mL), sensitivity (%), specificity (%) and AUC for determination of each biomarker.

TABLE 1

| Biomarker | Cut-off value | Sensitivity (%) | Specificity (%) | AUC |
|---|---|---|---|---|
| CXCL9 | 32.5 | 87 | 49 | 0.72 |
| CXCL10 | 287.1 | 60 | 80 | 0.75 |

From Table 1, in the determination based on each value of CXCL9 concentration and CXCL10 concentration in the serum, it was proved that the value of AUC was 0.7 or more, CXCL9 and CXCL10 in the serum were biomarkers useful for discrimination between CTD-ILD and IPAF. Conventionally, a diagnosis of CTD-ILD has been made based on diagnostic criteria for collagen disease, and a diagnosis of IPAF has been made based on diagnostic criteria proposed by ERS and ATS. These diagnostic criteria have included subjective factors such as physician findings and diagnostic imaging. However, the above results indicated that the concentrations of CXCL9 and CXCL10 in biological samples, which are objective indices, can serve as indices for discriminating between CTD-ILD and IPAF.

(2) Discrimination Between IPAF and IPF

For the serum CXCL10 concentration, an optimal cut-off value for distinguishing between the IPAF group (35 patients) and the IPF group (51 patients) in Example 1 was determined by ROC analysis. The sensitivity, specificity and AUC for determination using the set cut-off value were calculated. In this determination, when the concentration of CXCL10 was greater than or equal to the cut-off value, the patient was determined to have IPAF. When the concentration of CXCL10 was lower than the cut-off value, the patient was determined not to have IPAF. The obtained ROC curve is shown in FIG. 9. Table 2 shows the cut-off value (pg/mL), sensitivity (%), specificity (%) and AUC for determination of CXCL10.

TABLE 2

| Biomarker | Cut-off value | Sensitivity (%) | Specificity (%) | AUC |
|---|---|---|---|---|
| CXCL10 | 226.6 | 40 | 96 | 0.67 |

From Table 2, it was found that the value of AUC was about 0.7 in the determination based on the serum CXCL10 concentration, and the value of the serum CXCL10 concentration could also discriminate between IPAF and IPF. The specificity was particularly high in this determination, suggesting that the serum CXCL10 is useful for excluding patients suspected of having IPF in discrimination between IPAF and IPF.

Figure 10A:
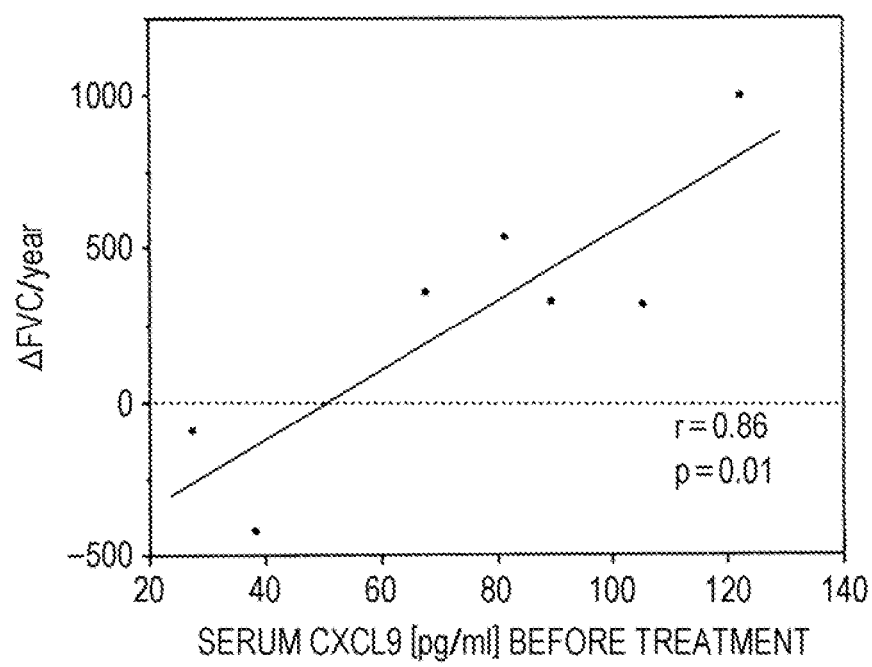
FIG. 10A is a graph showing the correlation between serum CXCL9 concentration before treatment with anti-inflammatory therapy and one-year forced vital capacity recovery (ΔFVC) for IPAF patients.
Figure 10B:
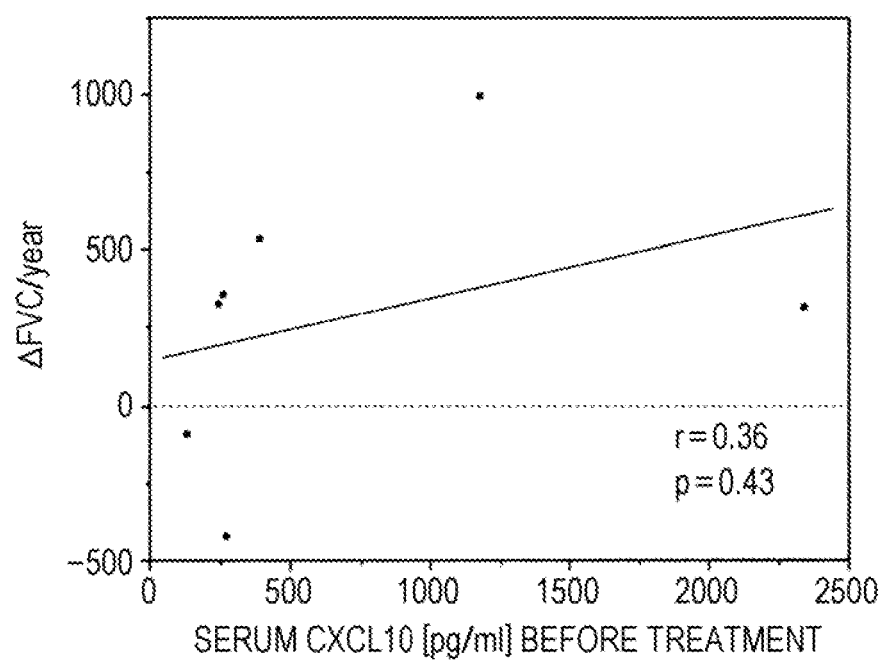
FIG. 10B is a graph showing the correlation between serum CXCL10 concentration before treatment with anti-inflammatory therapy and one-year forced vital capacity recovery (ΔFVC) for IPAF patients.

As shown in FIG. 10A, when IPAF patients were plotted with serum CXCL9 concentration before treatment with anti-inflammatory therapy on the horizontal axis, and with one-year forced vital capacity recovery (ΔFVC) on the vertical axis, a significant negative correlation was observed between the serum CXCL9 concentration and ΔFVC. This suggested that patients with high serum CXCL9 concentrations had high treatment responsiveness to anti-inflammatory therapy. Further, as shown in FIG. 10B, while a statistical correlation could not be obtained also with respect to the serum CXCL10 concentration, the forced vital capacity recovery was not observed in patients with low values, thus the same tendency is observed.

Example 3

(1) Biological Sample

The sera of the interstitial pneumonia patients in Example 1 were used as biological samples.

(2) Measurement of Biomarkers (2.1) Measurement of CXCL9 and CXCL10

The measured values acquired in Example 1 were used as the serum CXCL9 and CXCL10 concentration values of each patient.

(2.2) Measurement of KL-6

The serum KL-6 concentration of each patient was measured using HISCL-5000 or HISCL-2000i (Sysmex Corporation) using a HISCL KL-6 reagent (Sekisui Medical Co., Ltd.). The measurement procedure of KL-6 was similar to the measurement of CXCL9 in Example 1. The HISCL KL-6 reagent included an R1 reagent containing biotin-labeled mouse anti-KL-6 monoclonal antibody, an R2 reagent containing STA-bound magnetic particles, an R3 reagent containing ALP-labeled mouse anti-KL-6 monoclonal antibody, a HISCL R4 reagent as a measurement buffer solution, and a HISCL R5 reagent containing CDP-Star (registered trademark), a HISCL washing solution, and a KL-6 calibrator.

(2.3) Measurement of MMP9

The serum MMP9 concentration of each patient in Example 1 was measured by enzyme-linked immunosorbent assay (ELISA). The measurement procedure of MMP9 was as follows. An anti-MMP9 mouse monoclonal antibody sensitized to a 96-well plate at 0.5 μg/mL was reacted with serum (100 μL) diluted 5-fold with a specimen diluent for 2 hours. After washing 6 times with a HISCL washing solution (300 μL), 100 μL of a biotinylated goat anti-human MMP9 antibody (0.1 μg/mL, 1% BSA 0.5% casein TEA pH 7.4) was added thereto, and the mixture was reacted for 2 hours. After washing 6 times with a HISCL washing solution (300 μL), 100 μL of streptavidin ALP was added thereto, and the mixture was reacted for 20 minutes. After washing 6 times with a HISCL washing solution (300 μL), 100 μL of the R4 and R5 reagents mixed at 1:2 were added thereto, and the luminescent signal was counted using a plate reader. R & D Systems Duoset DY911 was used as the anti-MMP9 antibody.

(3) Discrimination Between IPAF and IPF

Multiple logistic regression analysis was performed using the serum CXCL9, CXCL10, KL-6 and MMP9 concentrations as explanatory variables. For this analysis, SPSS Statistics version 22.0 (IBM Corporation) was used. For a combination of CXCL9 and KL-6, a combination of CXCL9 and MMP9, a combination of CXCL10 and KL-6, and a combination of CXCL10 and MMP9, an optimal cut-off value for distinguishing between the IPAF group (35 patients) and the IPF group (51 patients) in Example 1 was determined. The sensitivity, specificity and AUC for determination using the set cut-off value were calculated. In this determination, when the predicted value P obtained by multiple logistic regression analysis was greater than or equal to the cut-off value, the patient was determined to have IPAF. Moreover, when the predicted value P was lower than the cut-off value, the patient was determined not to have IPAF. The obtained ROC curves are shown in FIGS. 11 to 14. Table 3 shows the cut-off value, sensitivity (%), specificity (%) and AUC for determination.

TABLE 3

| Biomarker | Cut-off value | Sensitivity (%) | Specificity (%) | AUC |
|---|---|---|---|---|
| CXCL9 and KL-6 | 0.37 | 91 | 35 | 0.64 |
| CXCL9 and MMP9 | 0.49 | 54 | 81 | 0.67 |
| CXCL10 and KL-6 | 0.44 | 49 | 83 | 0.68 |
| CXCL10 and MMP9 | 0.42 | 71 | 75 | 0.76 |

From Table 3, the AUC value was about 0.7 in the determination based on any combination of biomarkers. It was indicated that the combination can serve as an index for discrimination between IPAF and IPF.

What is claimed is:

1. A method for treating an interstitial pneumonia with autoimmune features (IPAF) patient with anti-inflammatory therapy, comprising:
    measuring at least one biomarker in a biological sample of an IPAF patient, wherein the biomarker is CXCL9;
    comparing a measured value of CXCL9 with a predetermined threshold value;
    determining that the patient may be responsive to an anti-inflammatory treatment based on a result of the comparing step, wherein the result comprises the measured value of CXCL9 being greater than or equal to a predetermined threshold value; and
    treating the patient with the anti-inflammatory therapy based on the result of the comparing step, wherein the result comprises the measured value of CXCL9 being greater than or equal to the predetermined threshold value.

2. The method according to claim 1, wherein the anti-inflammatory therapy comprises administering an immunosuppressant to the patient.

3. The method according to claim 2, wherein the immunosuppressant is a steroid.

4. The method according to claim 1, wherein the biological sample is a blood sample.

* * * * *